(12) United States Patent
Sharp et al.

(10) Patent No.: US 8,853,181 B2
(45) Date of Patent: Oct. 7, 2014

(54) FIDGETIN-LIKE 2 AS A TARGET TO ENHANCE WOUND HEALING

(75) Inventors: David J. Sharp, Scarsdale, NY (US); Rabab Charafeddine, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 54 days.

(21) Appl. No.: 13/553,155

(22) Filed: Jul. 19, 2012

(65) Prior Publication Data
US 2013/0022667 A1 Jan. 24, 2013

Related U.S. Application Data

(60) Provisional application No. 61/510,172, filed on Jul. 21, 2011.

(51) Int. Cl.
| | | |
|---|---|---|
| *A01N 43/04* | (2006.01) | |
| *C12P 19/34* | (2006.01) | |
| *C12N 15/58* | (2006.01) | |
| *C07H 21/02* | (2006.01) | |
| *C07H 21/04* | (2006.01) | |

(52) U.S. Cl.
USPC ............. 514/44; 435/6; 435/91.1; 435/91.31; 435/458; 536/23.1; 536/24.5

(58) Field of Classification Search
USPC .................. 435/6.1, 91.1, 91.31, 455, 6, 458; 514/44; 536/23.1, 24.5, 24.31
See application file for complete search history.

(56) References Cited

U.S. PATENT DOCUMENTS

2009/0004668 A1* 1/2009 Chen et al. ........................ 435/6

FOREIGN PATENT DOCUMENTS

WO    WO 02/44321    *    6/2002

OTHER PUBLICATIONS

Crooke, S., Ann. Rev. Medicine, vol. 55, pp. 61-95 (2004).*
Peracchi et al., Rev. Med. Virol., vol. 14, pp. 47-54 (2004).*
Agrawal et al., Molecular Med. Today, vol. 6, pp. 72-81 (2000).*
Chirila et al., Biomaterials, vol. 23, pp. 321-342 (2002).*
Doench et al., Genes and Development, vol. 17, pp. 438-443 (2003).*
Holen et al., Nucleic Acids Res., vol. 30, No. 8, pp. 1757-1766 (2002).*
Opalinska et al., Nature Rev., vol. 1, pp. 503-514 (2002).*
Mukherjee S. et al. "Human Fidgetin is a Microtubule Severing the Enzyme and Minus-End Depolymerase that Regulates Mitosis," Cell Cycle. Jun. 15, 2012; 11(12):2359. Epub Jun. 15, 2012 (Abstract).
Yang Y. et al. "Functional Characterization of Fidgetin, an AAA-Family Protein Mutated in Fidget Mice," Exp. Cell Res. Mar. 10, 2005; 304(1):50. Epub Dec. 10, 2004 (Abstract).
Mukherjee, S. et al. "Mammalian Fisgetin Proteins in Cell Migration and Morphogenesis," Mol. Cell. Biol. 21:126/B202, Meetings Abstract (Dec. 11, 2010).

* cited by examiner

*Primary Examiner* — Jane Zara
(74) *Attorney, Agent, or Firm* — Amster, Rothstein & Ebenstein LLP

(57) ABSTRACT

Methods of treating a wound in a subject are provided comprising administering to the subject an amount of an inhibitor of Fidgetin-like 2. Compositions and pharmaceutical compositions comprising an amount of an inhibitor of Fidgetin-like 2 are also provided. Methods are also provided for identifying an inhibitor of Fidgetin-like 2.

15 Claims, 13 Drawing Sheets

```
                        SEQUENCE LISTING

<160> NUMBER OF SEQ ID NOS: 12

<210> SEQ ID NO 1
<211> LENGTH: 4711
<212> TYPE: DNA
<213> ORGANISM: HOMO SAPIENS

<400> SEQUENCE: 1
agtgagctat ggggacacta ctgcactgta gcctgggcaa cagagcaaga ccttgtctca      60
aaaatgtata tatattttgg gctttttttc ctaaaacggg aactacaaca gcatatttgc     120
gagctgatga gagtgaccca gcagagaggg aaatggatca gctctgttga agatgcactg     180
gacaccagaa cacgcccagc ccctcaacca gtggccagag cagcacctgg acgtctcctc     240
caccaccccg tcgccggccc acaagttgga gttgccccct gggggtcgcc aacgctgcca     300
ctacgcttgg gcacacgacg acatctcagc cctcactgcc tccaacctcc taaagcgcta     360
tgcagagaag tactctgggg tcttggattc tccctacgag cgtccggccc tgggcgggta     420
cagcgacgcc tccttcctca acggcgccaa aggggatccc gagccctggc cagggccgga     480
gccaccctac cccttggcct cactccacga aggcctccca ggaaccaaat cgggcggtgg     540
cggcggttcc ggggccctgg ggggctcccc agttttagcc gggaacctcc ctgaaccccct    600 ctacgccggc aatgcgtgcg ggggcccatc ggcggcgccc gagtacgcgg ccggctacgg     660 cgggggtac ctggcgccgg gttactgcgc gcagacgggc gccgcgctgc ccccgccgcc      720
cccggccgcg ctcctgcagc ccccaccgcc tccggggtac gggccctcag cgccgctgta     780
caactatccc gcaggggct acgcagcgca gcccggctat ggcgcgctcc cgccgccccc      840
aggcccaccc ccggccccct acctgacccc gggcctgccc gcgcccacgc ccctgcccgc     900
gccggcaccg cccaccgcct atggcttccc cacggccgcg ccgggtgccg aatccgggct     960
gtcgctgaag cgcaaggccg ccgacgaggg gcccgagggc cgctaccgca agtacgcgta    1020
cgagcccgcc aaggccccccg tggctgacgg agcctcctac cccgccgcgg acaacggcga   1080
atgtcggggc aacgggttcc gggccaagcc gccaggagcc gcggaggagg cgtcgggcaa    1140
gtacggtggc ggcgtccccc tcaaggtcct gggctccccc gtctacggcc gcaactgga    1200 gcccttttgaa aagttcccgg agcgggcccc ggctcctcgt gggggttcg ccgtgccgtc    1260 gggggagact cccaaaggcg tggaccctgg ggccctggag ctggtgacga gcaagatggt    1320
ggactgcggg cccccggtgc agtgggcgga tgtggcgggc cagggcgcgc tcaaggcggc    1380
gctggaggag gagctggtgt ggccccctgct caggccgccc gctacccgg gcagcctgcg    1440 cccgccgcgg accgtcctgc tctttgggcc gcggggcgcg gcaaagcgc tgctgggccg    1500 ctgcctcgcc acgcagctgg gcgccacgct gttgcgcctg gcggcgcga ccctggctgc    1560 gcccggcgcc gccgagggcg cgcgcctcct ccaggccgcc ttcgcggccg cgcgctgccg    1620
cccaccctcc gtactcctca tcagcgagct agaggcgctg ctccccgccc gggacgacgg    1680
cgcggcggca ggggcgcgc tgcaggtgcc gctcctggcc tgcctggacg gggctgcgg    1740 cgcggggct gacggcgtgc tggttgtggg caccacctcg cggcccgcgg ctctggacga    1800 ggcgaccccgc cggcgcttct ctctccgctt ctacgtggcg ctgcccgaca gcccggcccg    1860
cgggcagatc ctgcagcggg cgctggccca gcaggcgctgc gcgctcagtg agcgggaact    1920
```

```
ggcggcgctg gtgcagggca cgcagggctt ctctggggc gagctggggc agctgtgcca      1980
gcaggcggcg gccggggcgg gcctcccggg gctgcagcgc cccctctcct acaaggacct      2040
ggaggcggcg ctggccaagg tgggccctag ggcctctgcc aaggaactgg actcgttcgt      2100
ggagtgggac aaaatgtacg gctccggaca ctgacgcgc gcggggagg ccgcgggagc       2160 cgcagtccct ccgtccccgc cgcctccgcg tgggagggat gtcactgact aaacccggct      2220 ggcagggct ggagtggtga atgtgggatc ggggacagga ggggtctgcc ggtggatatt       2280
ttttttttcg tgggaaggaa aatgcttctg ccaggcagat gccatatgcg ccgtgtactc      2340 aggttttcc tatttattgt ggactggaag ctcgccatct ccgcccggca gaccgggcag       2400
atccggcatg ggctggcacc cggggcctta agaactcctg ctctcttgcc acaacgcttt      2460
tgtctcctcg ctatctgaat ggcaccctcc ttctccctca ctctctccat cccattctct      2520
gcattctctt ggttttctct ccctttgct ttgtcgctga caccctgcc cacccatgc        2580 tggccctgtt tctctcctgc ccctcccctcc ccagctctcc atcccctcacc ctctgtgctt    2640 ctgtctccat ccctggctct ccagcgtccc tggccttttg gtccctgagc tttaatgcct     2700
ttccctgcct tctgttctta tttggactgc agtggccctt tgcaggagct ctggaggccc     2760
aggggctgag gaggagggtt acccctctac ccatctgaaa cctagggtct aggggatca      2820 aggaaaaaaa gtccccaaag aaggggaatt ttttgtttgt ttttgagggg agatcccaga     2880
aatgtagctt gtttcatatt ttagtcttct tattttgta aaatgtgtag aatttgctgt      2940 ttttctttt cttttgacaa ctcaggaaga aactgacctc agaagaatg ttagactttg       3000 gctgctctcc tgtgtgcccc tcacacctgc ccctccccc ccactccatc caggggacca      3060
aattctccca gacactcaaa aaatgagact tacggggaag gggagaggaa gacccagagg     3120
cctcagtgaa accccagcta ttcctggtca gaagcagaat gtattcctaa gggcttcctc     3180
cccagggccg aggcctaggc atgaatgtgg ggagtgggct gtggggtttg agagaaggga    3240
ggccttattc ctctcctgct gctccccacc ccctgcccca cccaacccct ccgctgagtg     3300
ttttctgtga agggctatcc agagttagga tgcccttgcc caattccttc ctgagaccca    3360
gaaggtaggg tgggagggcc caaatgggaa ggtgacctaa gcagaaagtc tccagaaagg    3420
tcatgtcccc tggccctgcc ttggcagagg tccccagtga cttatgctag gaggattcca    3480
tctgggtaga cagtctggcc acaaaatcag ctactgacc tcagccatct ctgctggagg     3540
ctctgaggag gagtgagcat ccctcacttg tgggggctct gtgaggaaat gtgccttccc   3600
cattcccccg gagtcctagg tctggagctc cagggctggg agagggtgag ggagatgggc    3660
aggggtgttt tctctgacct tgggggctta gtctcagtcc tgcctgaact ttccactagg    3720 cttgaaccc ttccaagaac catatttctc tccttcccac caattttccc ttgatgaggc     3780
tttagcagtt tgctcccacc accccccagcc catttcacaa ctctgatctt agtccaaagc    3840
aggggacacg ccccccccacc accacttttt ctctctccca tctcagcctc ctgtgcagtt   3900
ccttgcctgc ccgtgcattt cctagagtct actgcctccc cctggctgg gagggtgtct     3960 gggggggatc tttcagggc cctggcaccc agggcctgtg ctggcctagg agtgctgacc    4020
agaaggctgc tctgttcccc cccacccccg ttgcttctg gccccctctt tggagccagc     4080
cacccacagg gctttggtgc ctcagaagca gtgggctgcc gggtcacagc cgcaggctgc   4140
aaaagaccct cggagggagc atggagtgag gggttctctc tcaggtgtgt atgtattggg   4200
gggtgggggt gggtggaggg tgtcagggaa gttggggtgg gatcccagcc ttcccttcaa   4260
```

-continued

```
gaggcaggga gctctgggag gtggagtccc caccgctttc tctactaggc tcctcctgtt    4320
ccccaggctt ggggagcttt gcacaaggag actgccccca gcctagtggc acctacctca    4380
tgggctctgg ggcaggtagg ggaagggcca gtccagctct ggtaatgctg ggggaggca     4440 taccaaagaa tccaggggca gggagtgggg agggtgactt ccgagctggc ctctcccctt    4500
cctctaccca gactggggct gggatcctct cctcccgctg taaccatttc tacctcattt    4560
tgctgcgtgt tgtacatgga cgtatttatc tcctgtctga cgatgctctg cagttgtggt    4620
ctgtctacct cagaagagac tgtattttaa aagaaagtat tacacagtat taaagcgatg    4680
acatgtggtt tgcaaaaaaa aaaaaaaaaa a                                   4711
```

<210> SEQ ID NO 2
<211> LENGTH: 653
<212> TYPE: PRT
<213> ORGANISM: HOMO SAPIENS

<400> SEQUENCE: 2

```
Met His Trp Thr Pro Glu His Ala Gln Pro Leu Asn Gln Trp Pro Glu
1               5                   10                  15

Gln His Leu Asp Val Ser Ser Thr Thr Pro Ser Pro Ala His Lys Leu
            20                  25                  30

Glu Leu Pro Pro Gly Gly Arg Gln Arg Cys His Tyr Ala Trp Ala His
        35                  40                  45

Asp Asp Ile Ser Ala Leu Thr Ala Ser Asn Leu Leu Lys Arg Tyr Ala
    50                  55                  60

Glu Lys Tyr Ser Gly Val Leu Asp Ser Pro Tyr Glu Arg Pro Ala Leu
65                  70                  75                  80

Gly Gly Tyr Ser Asp Ala Ser Phe Leu Asn Gly Ala Lys Gly Asp Pro
                85                  90                  95

Glu Pro Trp Pro Gly Pro Glu Pro Pro Tyr Pro Leu Ala Ser Leu His
            100                 105                 110

Glu Gly Leu Pro Gly Thr Lys Ser Gly Gly Gly Gly Ser Gly Ala
        115                 120                 125

Leu Gly Gly Ser Pro Val Leu Ala Gly Asn Leu Pro Glu Pro Leu Tyr
    130                 135                 140

Ala Gly Asn Ala Cys Gly Gly Pro Ser Ala Ala Pro Glu Tyr Ala Ala
145                 150                 155                 160

Gly Tyr Gly Gly Gly Tyr Leu Ala Pro Gly Tyr Cys Ala Gln Thr Gly
                165                 170                 175

Ala Ala Leu Pro Pro Pro Pro Ala Ala Leu Leu Gln Pro Pro
            180                 185                 190

Pro Pro Gly Tyr Gly Pro Ser Ala Pro Leu Tyr Asn Tyr Pro Ala Gly
        195                 200                 205

Gly Tyr Ala Ala Gln Pro Gly Tyr Gly Ala Leu Pro Pro Pro Gly
    210                 215                 220

Pro Pro Pro Ala Pro Tyr Leu Thr Pro Gly Leu Pro Ala Pro Thr Pro
225                 230                 235                 240

Leu Pro Ala Pro Ala Pro Pro Thr Ala Tyr Gly Phe Pro Thr Ala Ala
                245                 250                 255

Pro Gly Ala Glu Ser Gly Leu Ser Leu Lys Arg Lys Ala Ala Asp Glu
            260                 265                 270

Gly Pro Glu Gly Arg Tyr Arg Lys Tyr Ala Tyr Glu Pro Ala Lys Ala
        275                 280                 285

Pro Val Ala Asp Gly Ala Ser Tyr Pro Ala Ala Asp Asn Gly Glu Cys
```

-continued

```
                290                 295                 300
Arg Gly Asn Gly Phe Arg Ala Lys Pro Pro Gly Ala Glu Glu Ala
305                 310                 315                 320

Ser Gly Lys Tyr Gly Gly Val Pro Leu Lys Val Leu Gly Ser Pro
                325                 330                 335

Val Tyr Gly Pro Gln Leu Glu Pro Phe Glu Lys Phe Pro Glu Arg Ala
                340                 345                 350

Pro Ala Pro Arg Gly Gly Phe Ala Val Pro Ser Gly Glu Thr Pro Lys
                355                 360                 365

Gly Val Asp Pro Gly Ala Leu Glu Leu Val Thr Ser Lys Met Val Asp
                370                 375                 380

Cys Gly Pro Pro Val Gln Trp Ala Asp Val Ala Gly Gln Gly Ala Leu
385                 390                 395                 400

Lys Ala Ala Leu Glu Glu Glu Leu Val Trp Pro Leu Leu Arg Pro Pro
                405                 410                 415

Ala Tyr Pro Gly Ser Leu Arg Pro Pro Arg Thr Val Leu Leu Phe Gly
                420                 425                 430

Pro Arg Gly Ala Gly Lys Ala Leu Leu Gly Arg Cys Leu Ala Thr Gln
                435                 440                 445

Leu Gly Ala Thr Leu Leu Arg Leu Arg Gly Ala Thr Leu Ala Ala Pro
                450                 455                 460

Gly Ala Ala Glu Gly Ala Arg Leu Leu Gln Ala Phe Ala Ala Ala
465                 470                 475                 480

Arg Cys Arg Pro Pro Ser Val Leu Leu Ile Ser Glu Leu Glu Ala Leu
                485                 490                 495

Leu Pro Ala Arg Asp Asp Gly Ala Ala Ala Gly Gly Ala Leu Gln Val
                500                 505                 510

Pro Leu Leu Ala Cys Leu Asp Gly Gly Cys Gly Ala Gly Ala Asp Gly
                515                 520                 525

Val Leu Val Val Gly Thr Thr Ser Arg Pro Ala Ala Leu Asp Glu Ala
                530                 535                 540

Thr Arg Arg Arg Phe Ser Leu Arg Phe Tyr Val Ala Leu Pro Asp Ser
545                 550                 555                 560

Pro Ala Arg Gly Gln Ile Leu Gln Arg Ala Leu Ala Gln Gly Cys
                565                 570                 575

Ala Leu Ser Glu Arg Glu Leu Ala Ala Leu Val Gln Gly Thr Gln Gly
                580                 585                 590

Phe Ser Gly Gly Glu Leu Gly Gln Leu Cys Gln Gln Ala Ala Ala Gly
                595                 600                 605

Ala Gly Leu Pro Gly Leu Gln Arg Pro Leu Ser Tyr Lys Asp Leu Glu
                610                 615                 620

Ala Ala Leu Ala Lys Val Gly Pro Arg Ala Ser Ala Lys Glu Leu Asp
625                 630                 635                 640

Ser Phe Val Glu Trp Asp Lys Met Tyr Gly Ser Gly His
                645                 650
```

<210> SEQ ID NO 3
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN FIDGETIN-LIKE 2

<400> SEQUENCE: 3
uuacacagua uuaaagcgau u          21

<210> SEQ ID NO 4
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN FIDGETIN-LIKE
      2

<400> SEQUENCE: 4
ucgcuuuaau acuguguaau u          21

<210> SEQ ID NO 5
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN FIDGETIN-LIKE
      2

<400> SEQUENCE: 5
caucugaaac cuagggucuu u          21

<210> SEQ ID NO 6
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN FIDGETIN-LIKE
      2

<400> SEQUENCE: 6
agacccuagg uuucagaugu u          21

<210> SEQ ID NO 7
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN FIDGETIN-LIKE
      2

<400> SEQUENCE: 7
gugacuuaug cuaggaggau u          21

<210> SEQ ID NO 8
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN FIDGETIN-LIKE
      2

<400> SEQUENCE: 8
uccuccuagc auaagucacu u          21

<210> SEQ ID NO 9
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN FIDGETIN-LIKE
      2

<400> SEQUENCE: 9
ggucagaagc agaauguauu u          21

```
<210> SEQ ID NO 10
<211> LENGTH: 21
<212> TYPE: RNA
<213> ORGANISM: ARTIFICIAL SEQUENCE
<220> FEATURE:
<223> OTHER INFORMATION: STRAND OF SIRNA DIRECTED TO HUMAN FIDGETIN-LIKE
      2

<400> SEQUENCE: 10
auacauucug cuucugaccu u                                              21

<210> SEQ ID NO 11
<211> LENGTH: 759
<212> TYPE: PRT
<213> ORGANISM: HOMO SAPIENS

<400> SEQUENCE: 11

Met Ile Ser Ser Thr Ser Val Tyr Gly Leu Lys Met Gln Trp Thr Pro
1               5                   10                  15

Glu His Ala Gln Trp Pro Glu Gln His Phe Asp Ile Thr Ser Thr Thr
            20                  25                  30

Arg Ser Pro Ala His Lys Val Glu Ala Tyr Arg Gly His Leu Gln Arg
        35                  40                  45

Thr Tyr Gln Tyr Ala Trp Ala Asn Asp Asp Ile Ser Ala Leu Thr Ala
    50                  55                  60

Ser Asn Leu Leu Lys Lys Tyr Ala Glu Lys Tyr Ser Gly Ile Leu Glu
65                  70                  75                  80

Gly Pro Val Asp Arg Pro Val Leu Ser Asn Tyr Ser Asp Thr Pro Ser
                85                  90                  95

Gly Leu Val Asn Gly Arg Lys Asn Glu Ser Glu Pro Trp Gln Pro Ser
            100                 105                 110

Leu Asn Ser Glu Ala Val Tyr Pro Met Asn Cys Val Pro Asp Val Ile
        115                 120                 125

Thr Ala Ser Lys Ala Gly Val Ser Ser Ala Leu Pro Pro Ala Asp Val
    130                 135                 140

Ser Ala Ser Ile Gly Ser Ser Pro Gly Val Ala Ser Asn Leu Thr Glu
145                 150                 155                 160

Pro Ser Tyr Ser Ser Thr Cys Gly Ser His Thr Val Pro Ser Leu
                165                 170                 175

His Ala Gly Leu Pro Ser Gln Glu Tyr Ala Pro Gly Tyr Asn Gly Ser
            180                 185                 190

Tyr Leu His Ser Thr Tyr Ser Gln Pro Ala Pro Ala Leu Pro Ser
        195                 200                 205

Pro His Pro Ser Pro Leu His Ser Ser Gly Leu Leu Gln Pro Pro Pro
    210                 215                 220

Pro Pro Pro Pro Pro Ala Leu Val Pro Gly Tyr Asn Gly Thr Ser
225                 230                 235                 240

Asn Leu Ser Ser Tyr Ser Tyr Pro Ser Ala Ser Tyr Pro Pro Gln Thr
                245                 250                 255

Ala Val Gly Ser Gly Tyr Ser Pro Gly Gly Ala Pro Pro Pro Ser
            260                 265                 270

Ala Tyr Leu Pro Ser Gly Ile Pro Ala Pro Thr Pro Leu Pro Pro Thr
        275                 280                 285

Thr Val Pro Gly Tyr Thr Tyr Gln Gly His Gly Leu Thr Pro Ile Ala
    290                 295                 300
```

-continued

```
Pro Ser Ala Leu Thr Asn Ser Ser Ala Ser Ser Leu Lys Arg Lys Ala
305                 310                 315                 320

Phe Tyr Met Ala Gly Gln Gly Asp Met Asp Ser Ser Tyr Gly Asn Tyr
                325                 330                 335

Ser Tyr Gly Gln Gln Arg Ser Thr Gln Ser Pro Met Tyr Arg Met Pro
            340                 345                 350

Asp Asn Ser Ile Ser Asn Thr Asn Arg Gly Asn Gly Phe Asp Arg Ser
                355                 360                 365

Ala Glu Thr Ser Ser Leu Ala Phe Lys Pro Thr Lys Gln Leu Met Ser
    370                 375                 380

Ser Glu Gln Gln Arg Lys Phe Ser Ser Gln Ser Ser Arg Ala Leu Thr
385                 390                 395                 400

Pro Pro Ser Tyr Ser Thr Ala Lys Asn Ser Leu Gly Ser Arg Ser Ser
                405                 410                 415

Glu Ser Phe Gly Lys Tyr Thr Ser Pro Val Met Ser Glu His Gly Asp
                420                 425                 430

Glu His Arg Gln Leu Leu Ser His Pro Met Gln Gly Pro Gly Leu Arg
        435                 440                 445

Ala Ala Thr Ser Ser Asn His Ser Val Asp Glu Gln Leu Lys Asn Thr
450                 455                 460

Asp Thr His Leu Ile Asp Leu Val Thr Asn Glu Ile Ile Thr Gln Gly
465                 470                 475                 480

Pro Pro Val Asp Trp Asn Asp Ile Ala Gly Leu Asp Leu Val Lys Ala
                485                 490                 495

Val Ile Lys Glu Glu Val Leu Trp Pro Val Leu Arg Ser Asp Ala Phe
            500                 505                 510

Ser Gly Leu Thr Ala Leu Pro Arg Ser Ile Leu Leu Phe Gly Pro Arg
    515                 520                 525

Gly Thr Gly Lys Thr Leu Leu Gly Arg Cys Ile Ala Ser Gln Leu Gly
530                 535                 540

Ala Thr Phe Phe Lys Ile Ala Gly Ser Gly Leu Val Ala Lys Trp Leu
545                 550                 555                 560

Gly Glu Ala Glu Lys Ile Ile His Ala Ser Phe Leu Val Ala Arg Cys
                565                 570                 575

Arg Gln Pro Ser Val Ile Phe Val Ser Asp Ile Asp Met Leu Leu Ser
            580                 585                 590

Ser Gln Val Asn Glu Glu His Ser Pro Val Ser Arg Met Arg Thr Glu
    595                 600                 605

Phe Leu Met Gln Leu Asp Thr Val Leu Thr Ser Ala Glu Asp Gln Ile
610                 615                 620

Val Val Ile Cys Ala Thr Ser Lys Pro Glu Glu Ile Asp Glu Ser Leu
625                 630                 635                 640

Arg Arg Tyr Phe Met Lys Arg Leu Leu Ile Pro Leu Pro Asp Ser Thr
                645                 650                 655

Ala Arg His Gln Ile Ile Val Gln Leu Leu Ser Gln His Asn Tyr Cys
            660                 665                 670

Leu Asn Asp Lys Glu Phe Ala Leu Leu Val Gln Arg Thr Glu Gly Phe
            675                 680                 685

Ser Gly Leu Asp Val Ala His Leu Cys Gln Glu Ala Val Val Gly Pro
    690                 695                 700

Leu His Ala Met Pro Ala Thr Asp Leu Ser Ala Ile Met Pro Ser Gln
705                 710                 715                 720

Leu Arg Pro Val Thr Tyr Gln Asp Phe Glu Asn Ala Phe Cys Lys Ile
```

```
            725                 730                 735
Gln Pro Ser Ile Ser Gln Lys Glu Leu Asp Met Tyr Val Glu Trp Asn
        740                 745                 750
Lys Met Phe Gly Cys Ser Gln
        755

<210> SEQ ID NO 12
<211> LENGTH: 4535
<212> TYPE: DNA
<213> ORGANISM: HOMO SAPIENS

<400> SEQUENCE: 12
gggtttgaaa ttccaacatg gcagaggctg cagtccgtct tcccttcaaa aacttggaat      60
gatttcaaat cataggcacc ttcacttaac cctagcttcc attcatcagc aaacacatcg     120
gatcgatgct acgctaacct atcgggttct ctctccgcgc gttcaggtta aatgaatacc     180
tgacgaaagg gcccacgttt caaggcagtg acatttgata gctgagagga aaagtggctt     240
taatgaaaag caacctttgg aattcctgct tgtgagaaat ccaattcagc tttttgtgct     300
gccagcaaga aatgatcagt agcaccagtg tttatggctt gaagatgcag tggacgccag     360
agcatgccca gtggccagaa cagcactttg acatcacctc aaccactcgg tctcctgccc     420
acaaagttga agcctacaga ggtcatctgc agcgcaccta tcagtacgcc tgggcgaatg     480
atgacatatc tgctctgact gcatccaacc tactaaaaaa atatgcagag aagtattccg     540
gcattttgga aggtcctgtg accgacccg tactcagcaa ctattcggac acaccatcag     600
gactagtgaa cggtcggaaa atgaaagtg aaccctggca gccttccttg aattcagaag     660
ctgtttatcc catgaactgt gttccggatg ttatcactgc agcaaagct ggagtcagtt     720 cagcccctcc tccagcagat gtctctgcga gtataggaag ctctcctggg gtagccagca     780
acctgacaga acctagttat tcaagtagta cctgtggaag ccacactgta cccagtcttc     840
atgcagggct cccatctcag gaatatgccc aggatacaa cggatcatat ttgcattcta     900
cttatagtag ccagccagca cctgcacttc cttcacctca tccgtctcct ttgcatagct     960
ctgggctact acagccccca ccaccactc tccgccacc agccttggtc ccaggctaca    1020
atgggacttc taacctctcc agttacagct atccgtctgc tagctatcct cctcagactg    1080
ctgtggggtc tgggtacagc cctggggggg caccgcctcc gccttcagcg tacctgcctt    1140
caggaattcc tgctcccacc cccctacccc ccaccactgt tcctggctac acctaccagg    1200
gccatggttt gacacctatt gcaccgtcgg ctctgacaaa cagttcagca agttctctca    1260
aaaggaaagc tttctacatg gcagggcaag agatatgga ctccagttat ggaaattaca    1320
gctatggcca acagagatct acacagagtc ctatgtacag aatgcccgac aacagcattt    1380
caaacacaaa tcgggggaat ggcttttgaca gaagtgctga acatcatcc ttagcattta    1440 agccaacgaa gcagctaatg tcctctgaac agcaaaggaa attcagcagc cagtccagta    1500
gggctctgac ccctccttcc tacagtactg ctaaaaattc attgggatca agatccagtg    1560
aatcctttgg gaagtacaca tcgccagtaa tgagtgagca tggggacgag cacaggcagc    1620
tcctctctca cccaatgcaa ggccctggac tccgtgcagc tacctcatcc aaccactctg    1680
tggacgagca actgaagaat actgacacgc acctcatcga cctggtaacc aatgagatta    1740
tcacccaagg acctccagtg gactggaatg acattgctgg tctcgacctg gtgaaggctg    1800
tcattaaaga ggaggtttta tggccagtgt tgaggtcaga cgcgttcagt ggactgacgg    1860
ccttacctcg gagcatcctt ttatttggac ctcgggggac aggcaaaaca ttattgggca    1920
```

```
gatgcatcgc tagtcagctg ggggccacat ttttcaaaat tgccggttct ggactagtcg    1980
ccaagtggtt aggagaagca gagaaaatta tccatgcctc ttttcttgtg gccaggtgtc    2040
gccagccctc ggtgattttt gttagtgaca ttgacatgct tctctcctct caagtgaatg    2100
aggaacatag tccagtcagt cggatgagaa ccgaatttct gatgcaactg gacactgtac    2160
taacttcggc tgaggaccaa atcgtagtaa tttgtgccac cagtaaacca gaagaaatag    2220
atgaatccct tcggaggtac ttcatgaaac gactttttaat cccacttcct gacagcacag    2280
cgaggcacca gataatagta caactgctct cacagcacaa ttactgtctc aatgacaagg    2340
agtttgcact gctcgtccag cgcacagaag gcttttctgg actagatgtg gctcatttgt    2400
gtcaggaagc agtggtgggc cccctccatg ccatgccagc cacagacctt tcagccatta    2460
tgcccagcca gttgaggccc gttacatatc aagactttga aaatgctttc tgcaagattc    2520
agcctagcat atctcaaaag gagcttgata tgtatgttga atggaacaaa atgtttggtt    2580
gcagtcagtg ataacttctt tagaaaaaaa aatgtaatg aatgttggca cacacacata    2640
aaacctgcta catagggaat agagccccctt tccagtagag tttaaattgc aaagggtact    2700
ggggaagatg acgattaagt tgcatcttta gagtcagggt agatttggag aaaagtgca     2760 tcaaatgaga gcttctgatt tgaaagcccc agatgacaga aagcatatgt ggatgctcag    2820
ttctgttcaa gctagacaac actcaccaag gagcaaggtg caagtgtgtt gatttcagaa    2880
ggacatgaac ctcgtgtgtt gattccattc tgctgttctc gagatttagt tgctgtcaag    2940
tgcctggagt ggtgctttat ttttttgtttg cctcacaatt acattggtgg catgtgctaa    3000
tataaagagc tttaacttca aacattattg gactaaagag atgaacagtt gtgttatgac    3060
agaaaaccag attttttgcca ttttaagagc aacagtattc ctcaatcctg tctgttctgc    3120
agtattaagc taagaacagg taaaacaggg taacggtaat ctggacctta atttctgcag    3180
ttcatttctt ttaatgttct tgtctgcaaa aactcaggaa agtgattgtg atttgtacag    3240
tacctcaaag gaatgtgttg aaagcactat gtactgctga gagtaatagg ataggcttca    3300
atgttacttt atattaaaat gtatgtttac ctcaacaatt ggaaaatagc aaggaaaatt    3360
actttgaatg tatccagaaa aatactgaag tgtgatacaa ctgaatatttт acagtttaaa    3420 gtagaaatgg aaggattttt ttaagttctt ttactaatta tggggaatta accagagcag    3480
aataattctt tatgtcaata actgcaagag ttcttagtac attgctccct tgataattaag    3540 tgaaatgtt cttaaaaggt acactggtta attgaaagct acttattcag tttgtgttag    3600
tgtctagacc tgtcagccac aagacctgtt taggaccctg aaagtcacag tacctaaaaa    3660
ctatgactgc ctttttattg cataggtggt agtggtggtg atggtggtgg tagtttgcaa    3720
gttatctctt aaaactgctg ggaatggtgt cattctattc actaatctag cttatagact    3780
tgccgtgctg tttgatagaa tgcagaggat agcaaccaaa acaaatacac aaataaataa    3840
aaacaaaaac caaccaacaa accaacttac atacacatat atatatccac aaagaacctc    3900
tccatctcct cccctttcttt ttgactccac tcttgtcagt gcaattttgc ttctcatttt    3960
gaaatctggg ctgtagtgct cctgctttat ttctacctca gttttgttac atttctcttg    4020
gaaagtaaag tagaaaattg gaagtggaca cacacactgc aatgtagctt gccaaacatg    4080
ttactttgtt ttcttccatc tttcaccgta aatctagttt ccaaagacat cagcatttgt    4140
gcttacttcc acctcagtct accagcccca cccctaccca tggcataagt ggcatttttc    4200
ttaatttcct atttttтctcc tgctctctgt caagttgttc tttgtatcct ttaatgcttt    4260
```

```
atgtgcaacc tttcattgat agtgggctga tgtttggcaa tgcttctgaa ctgtcacaga    4320
gcaggctgta gctttccaca gccactgccc atgcataagc agaacagcct ggccttttga    4380
atgtattttc ctgggttttt tcccctttt c tttttttagt ttagagatgc agtaacaaaa   4440
ctgttgcaaa gcactggcat tttatgtatt caataaataa gtgatgtaca ttttt aaaaa   4500 aatttaaata aatgcaatga gaagccccaa gaaag                               4535
```

FIDGETIN-LIKE 2 AS A TARGET TO ENHANCE WOUND HEALING

CROSS-REFERENCE TO RELATED APPLICATIONS

This application claims benefit of U.S. Provisional Application No. 61/510,172, filed Jul. 21, 2011, the contents of which are hereby incorporated by reference.

STATEMENT OF GOVERNMENT SUPPORT

This invention was made with government support under grant number GM065940 awarded by the National Institute of General Medical Sciences. The government has certain rights in the invention.

SEQUENCE LISTING INCORPORATION

The ".txt" Sequence Listing filed with this application by EFS and which is entitled 96700 1855 ST25.txt, is 26 kilobytes in size and which was created on Jun. 11, 2012, is hereby incorporated by reference.

BACKGROUND OF THE INVENTION

The disclosures of all publications, patents, patent application publications and books referred to in this application are hereby incorporated by reference in their entirety into the subject application to more fully describe the art to which the subject invention pertains.

The development of safe and effective therapies for treating acute and chronic wounds is an issue currently of great interest to clinical scientists and industry, alike. Wound healing is an intricate, multi-stage process that relies heavily on the delivery of new cells to the wound zone. Two key elements of the wound healing response are fibroplasia and epithelialization when fibroblasts and epithelial cells, respectively, enter the wound to form a protective barrier from the external environment. This is stimulated by cell proliferation and migration from the wound edge. The identification of agents that increase the rate at which cells invade and close a wound would represent a major advance in wound healing therapeutics. Ideally, this would be a topically applied agent that stimulates the proliferation and migration of fibroblasts and wound edge epithelial cells.

The present invention addresses this need and identifies a novel target in promoting wound healing and provides therapies and assays based thereon.

SUMMARY OF THE INVENTION

A method of treating a wound in a subject is provided comprising administering to the subject an amount of an inhibitor of Fidgetin-like 2 effective to treat the wound.

A pharmaceutical composition is provided comprising an amount of an inhibitor of Fidgetin-like 2.

A method for identifying a candidate agent for treating a wound comprising:
a) determining the activity of an amount of Fidgetin-like 2; and
b) contacting the amount of Fidgetin-like 2 with the candidate agent and determining the activity of the amount of Fidgetin-like 2 in the presence of the candidate agent,
wherein a decreased activity of the amount of Fidgetin-like 2 in the presence of the candidate agent as compared to the activity of Fidgetin-like 2 in the absence of the candidate agent indicates that the candidate agent can treat a wound, and wherein no change in or an increased activity of the amount of Fidgetin-like 2 in the presence of the candidate agent as compared to the activity of Fidgetin-like 2 in the absence of the candidate agent does not indicate that the candidate agent can treat a wound.

An inhibitor of Fidgetin-like 2 is provided for treating a wound or promoting wound healing.

BRIEF DESCRIPTION OF THE DRAWINGS

FIG. 1A shows a Western blot of human U2OS cell lysates probed with an anti-Fidgetin-like 2 antibody generated in-lab. This antibody recognizes a single band that is substantially decreased by Fidgetin-like 2 siRNA treatment (see FIG. 2 below). FIG. 1B shows a migrating U2OS cell double-labeled for Fidgetin-like 2 and microtubules. At high magnification (inset), Fidgetin-like 2 clearly co-localizes with spans of the microtubule lattice near the cell edge.

FIG. 2A shows Western blots of U2OS cell lysates obtained from control (N) and Fidgetin-like 2 siRNA treated cultures (72 hrs. after treatment). Actin was used as a loading control. FIG. 2B shows time-lapse phase contrast images of "wound healing" assays performed in control and Fidgetin-like 2 siRNA treated cultures. In these assays, a monolayer of U2OS cells is "wounded" by a pipette tip and the invasion of cells into the wound is monitored over time. FIG. 2C shows the average rate of wound closure in each condition which is increased nearly 4-fold after Fidgetin-like 2 siRNA. FIG. 2D shows the trajectories of single control and Fidgetin-like 2 siRNA treated cells as they enter the wound zone. Not only do Fidgetin-like 2 siRNA-treated cells move several-fold faster than controls, they also display more directionally persistent migration as indicated in FIG. 2E.

DETAILED DESCRIPTION OF THE INVENTION

Figure 1:
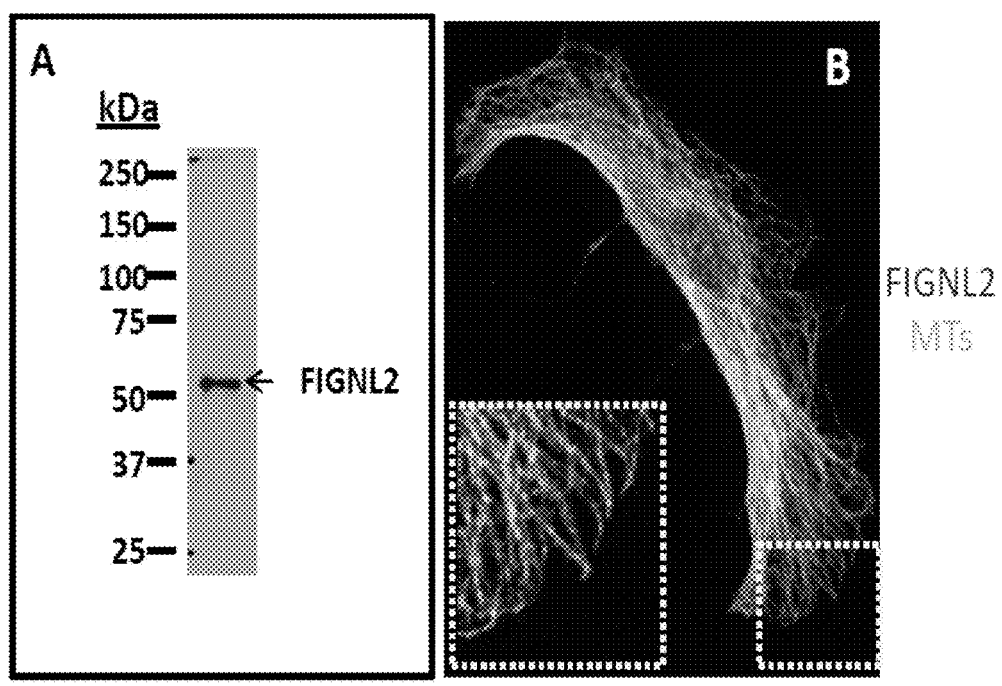
FIG. 1A-1B: Fidgetin-like 2 is expressed in human tissue culture cells where it localizes to microtubules.

A method of treating a wound in a subject is provided comprising administering to the subject an amount of an inhibitor of Fidgetin-like 2 effective to treat a wound.

In an embodiment, the amount of inhibitor of Fidgetin-like 2 is effective to accelerate wound healing.

In an embodiment, the inhibitor of Fidgetin-like 2 is administered locally to the wound. In an embodiment, the inhibitor of Fidgetin-like 2 is administered via a vein or artery. In an embodiment, the inhibitor of Fidgetin-like 2 is administered by injection, catheterization or cannulation. In an embodiment, the inhibitor of Fidgetin-like 2 is administered from an implant that elutes the inhibitor, for example a eluting stent or an eluting skin patch.

In an embodiment, the inhibitor of Fidgetin-like 2 is administered topically to the wound.

In an embodiment, the inhibitor of Fidgetin-like 2 is a nucleic acid. In an embodiment, the inhibitor of Fidgetin-like 2 is an siRNA or shRNA. In an embodiment, the nucleic acid is directed against a DNA encoding Fidgetin-like 2 or against an mRNA encoding Fidgetin-like 2.

In an embodiment of the method, the inhibitor of Fidgetin-like 2 is encapsulated in a nanoparticle. In an embodiment the nanoparticle is a liposomal nanoparticle.

In an embodiment, the Fidgetin-like 2 is human Fidgetin-like 2.

In an embodiment, the Fidgetin-like 2 comprises consecutive amino acid residues having the sequence set forth in SEQ ID NO:2.

In an embodiment, the wound is an epidermal wound. In an embodiment, the wound is a skin wound.

In an embodiment, the wound is a cardiac tissue wound. In an embodiment, the wound is a cardiovascular wound, for example resulting from a myocardial infarction.

In an embodiment, the wound is a neuronal wound.

A pharmaceutical composition is provided comprising an amount of an inhibitor of Fidgetin-like 2. In an embodiment, the pharmaceutical composition comprises an amount of an inhibitor of Fidgetin-like 2 effective to treat a wound in a human subject. In an embodiment, the wound is a skin wound. In an embodiment, the wound is an epidermal wound.

In an embodiment, the pharmaceutical composition comprises a pharmaceutically acceptable carrier.

In an embodiment of the pharmaceutical composition the inhibitor of Fidgetin-like 2 is a nucleic acid.

In an embodiment of the pharmaceutical composition the inhibitor of Fidgetin-like 2 is an siRNA or shRNA.

In an embodiment of the pharmaceutical composition the nucleic acid is directed against a DNA encoding Fidgetin-like 2 or against an mRNA encoding Fidgetin-like 2.

In an embodiment of the pharmaceutical composition, the inhibitor of Fidgetin-like 2 is encapsulated in a nanoparticle. In an embodiment the nanoparticle is a liposomal nanoparticle.

In an embodiment of the pharmaceutical composition the Fidgetin-like 2 is human Fidgetin-like 2.

In an embodiment of the pharmaceutical composition the Fidgetin-like 2 comprises SEQ ID NO:2.

A method for identifying a candidate agent for treating a wound comprising:
a) determining the activity of an amount of Fidgetin-like 2; and
b) contacting the amount of Fidgetin-like 2 with the candidate agent and determining the activity of the amount of Fidgetin-like 2 in the presence of the candidate agent,
wherein a decreased activity of the amount of Fidgetin-like 2 in the presence of the candidate agent as compared to the activity of Fidgetin-like 2 in the absence of the candidate agent indicates that the candidate agent can treat a wound, and wherein no change in or an increased activity of the amount of Fidgetin-like 2 in the presence of the candidate agent as compared to the activity of Fidgetin-like 2 in the absence of the candidate agent does not indicate that the candidate agent can treat a wound.

In an embodiment, the Fidgetin-like 2 is human Fidgetin-like 2.

In an embodiment, the Fidgetin-like 2 comprises SEQ ID NO:2.

In an embodiment, the candidate agent is a small molecule of 2000 Daltons or less. In an embodiment, the candidate agent is a small molecule of 1000 Daltons or less. In an embodiment, the candidate agent is a substituted or un-substituted hydrocarbon small molecule.

An inhibitor of Fidgetin-like 2 is provided for treating a wound or promoting wound healing.

In an embodiment, the inhibitor of Fidgetin-like 2 is a nucleic acid.

In an embodiment, the inhibitor is an siRNA or shRNA.

In an embodiment, the nucleic acid is directed against a DNA encoding Fidgetin-like 2 or against an mRNA encoding Fidgetin-like 2.

In an embodiment, the Fidgetin-like 2 is human Fidgetin-like 2.

In an embodiment, the Fidgetin-like 2 comprises SEQ ID NO:2.

In an embodiment, the inhibitor or the candidate agent is an aptamer, a nucleic acid, an oligonucleotide, or a small organic molecule of 2000 Daltons or less. In an embodiment, the inhibitor is cell-membrane permeable.

The dosage of the inhibitor administered in treatment will vary depending upon factors such as the pharmacodynamic characteristics of a specific inhibitor and its mode and route of administration; the age, sex, metabolic rate, absorptive efficiency, health and weight of the recipient; the nature and extent of the symptoms; the kind of concurrent treatment being administered; the frequency of treatment with the inhibitor and the desired therapeutic effect.

A dosage unit of the inhibitor may comprise a single compound, or a mixture of the compound with one or more anti-infection compound(s) or wound healing-promoting compound(s).

In an embodiment, the siRNA (small interfering RNA) as used in the methods or compositions described herein comprises a portion which is complementary to an mRNA sequence encoding a Fidgetin-like 2 protein. In an embodiment, the Fidgetin-like 2 protein is a human Fidgetin-like 2 protein. In an embodiment, the mRNA is encoded by the DNA sequence NCBI Reference Sequence: NM_001013690.4 (SEQ ID NO:1), and the siRNA is effective to inhibit expression of Fidgetin-like 2 protein. In an embodiment, the Fidgetin-like 2 protein comprises consecutive amino acid residues having the sequence set forth in SEQ ID NO:2.

In an embodiment, the siRNA comprises a double-stranded portion (duplex). In an embodiment, the siRNA is 20-25 nucleotides in length. In an embodiment the siRNA comprises a 19-21 core RNA duplex with a one or two nucleotide 3' overhang on, independently, either one or both strands. The siRNA can be 5' phosphorylated, or not, and may be modified with any of the known modifications in the art to improve efficacy and/or resistance to nuclease degradation. In an embodiment the siRNA can be administered such that it is transfected into one or more cells. In an embodiment, the siRNA is 5' phosphorylated.

In an embodiment, the 5' terminal residue of a strand of the siRNA is phosphorylated. In an embodiment the 5' terminal residue of the antisense strand of the siRNA is phosphorylated. In one embodiment, a siRNA of the invention comprises a double-stranded RNA wherein one strand of the double-stranded RNA is 80, 85, 90, 95 or 100% complementary to a portion of an RNA transcript of a gene encoding Fidgetin-like 2 protein. In an embodiment, the RNA transcript of a gene encoding Fidgetin-like 2 protein is an mRNA.

In an embodiment, the Fidgetin-like 2 protein is a human Fidgetin-like 2 protein. In an embodiment, a siRNA of the invention comprises a double-stranded RNA wherein one strand of the RNA comprises a portion having a sequence the same as a portion of 18-25 consecutive nucleotides of an RNA transcript of a gene encoding Fidgetin-like 2 protein. In an embodiment, the Fidgetin-like 2 protein is a human Fidgetin-like 2 protein. In yet another embodiment, a siRNA of the invention comprises a double-stranded RNA wherein both strands of RNA are connected by a non-nucleotide linker. Alternately, a siRNA of the invention comprises a double-stranded RNA wherein both strands of RNA are connected by a nucleotide linker, such as a loop or stem loop structure.

In one embodiment, a single strand component of a siRNA of the invention is from 14 to 50 nucleotides in length. In another embodiment, a single strand component of a siRNA of the invention is 14, 15, 16, 17, 18, 19, 20, 21, 22, 23, 24, 25, 26, 27, or 28 nucleotides in length. In yet another embodiment, a single strand component of a siRNA of the invention is 21 nucleotides in length. In yet another embodiment, a single strand component of a siRNA of the invention is 22 nucleotides in length. In yet another embodiment, a single strand component of a siRNA of the invention is 23 nucleotides in length. In one embodiment, a siRNA of the invention is from 28 to 56 nucleotides in length. In another embodiment, a siRNA of the invention is 40, 41, 42, 43, 44, 45, 46, 47, 48, 49, 50, 51, or 52 nucleotides in length.

In another embodiment, an siRNA of the invention comprises at least one 2'-sugar modification. In another embodiment, an siRNA of the invention comprises at least one nucleic acid base modification. In another embodiment, an siRNA of the invention comprises at least one phosphate backbone modification. As used herein, "at least one" means one or more.

In one embodiment, RNAi inhibition of Fidgetin-like 2 protein is effected by a short hairpin RNA ("shRNA"). The shRNA is introduced into the appropriate cell by transduction with a vector. In an embodiment, the vector is a lentiviral vector. In an embodiment, the vector comprises a promoter. In an embodiment, the promoter is a U6 or H1 promoter. In an embodiment the shRNA encoded by the vector is a first nucleotide sequence ranging from 19-29 nucleotides complementary to the target gene/mRNA, in the present case the mRNA encodes Fidgetin-like 2 protein. In an embodiment the Fidgetin-like 2 protein is a human Fidgetin-like 2 protein. In an embodiment the shRNA encoded by the vector also comprises a short spacer of 4-15 nucleotides (a loop, which does not hybridize) and a 19-29 nucleotide sequence that is a reverse complement of the first nucleotide sequence. In an embodiment the siRNA resulting from intracellular processing of the shRNA has overhangs of 1 or 2 nucleotides. In an embodiment the siRNA resulting from intracellular processing of the shRNA overhangs has two 3' overhangs. In an embodiment the overhangs are UU.

NCBI Reference Sequence: NM_001013690.4 (SEQ ID NO:1) (nucleic acid encoding Human Fidgetin-like 2)

```
  1 agtgagctat ggggacacta ctgcactgta gcctgggcaa cagagcaaga ccttgtctca
 61 aaaatgtata tatattttgg gcttttttc ctaaaacggg aactacaaca gcatatttgc
121 gagctgatga gagtgaccca gcagagaggg aaatggatca gctctgttga agatgcactg
181 gacaccagaa cacgcccagc ccctcaacca gtggccagag cagcacctgg acgtctcctc
241 caccaccccg tcgccggccc acaagttgga gttgccccct ggggtcgcc aacgctgcca
301 ctacgcttgg gcacacgacg acatctcagc cctcactgcc tccaacctcc taaagcgcta
```

```
-continued
 361 tgcagagaag tactctgggg tcttggattc tccctacgag cgtccggccc tgggcgggta
 421 cagcgacgcc tccttcctca acggcgccaa aggggatccc gagccctggc cagggccgga
 481 gccaccctac cccttggcct cactccacga aggcctccca ggaaccaaat cgggcggtgg
 541 cggcggttcc ggggccctgg ggggctcccc agttttagcc gggaacctcc ctgaacccct
 601 ctacgccggc aatgcgtgcg ggggcccatc ggcggcgccc gagtacgcgg ccggctacgg
 661 cgggggtac ctggcgccgg gttactgcgc gcagacgggc gccgcgctgc ccccgccgcc
 721 cccggccgcg ctcctgcagc cccaccgcc tccgggtac gggccctcag cgccgctgta
 781 caactatccc gcaggggct acgcagcgca gcccggctat ggcgcgctcc cgccgcccc
 841 aggcccaccc ccggccccct acctgacccc gggcctgccc gcgcccacgc ccctgcccgc
 901 gccggcaccg cccaccgcct atggcttccc cacggccgcg ccgggtgccg aatccgggct
 961 gtcgctgaag cgcaaggccg ccgacgaggg gcccgagggc cgctaccgca agtacgcgta
1021 cgagcccgcc aaggccccg tggctgacgg agcctcctac cccgccgcgg acaacggcga
1081 atgtcggggc aacgggttcc gggccaagcc gccaggagcc gcggaggagg cgtcgggcaa
1141 gtacggtggc ggcgtcccc tcaaggtcct gggctccccc gtctacgccc cgcaactgga
1201 gcccttttgaa aagttcccgg agcgggcccc ggctcctcgt gggggttcg ccgtgccgtc
1261 gggggagact cccaaaggcg tggacccggg ggccctggag ctggtgacga gcaagatggt
1321 ggactgcggg ccccggtgc agtgggcgga tgtggcgggc caggcgcgc tcaaggcggc
1381 gctggaggag gagctggtgt ggcccctgct caggccgccc gcctaccgg gcagcctgcg
1441 cccgccgcgg accgtcctgc tctttgggcc gcggggcgcg ggcaaagcgc tgctgggccg
1501 ctgcctcgcc acgcagctgg gcgccacgct gttgcgcctg cgcggcgcga ccctggctgc
1561 gcccggcgcc gccgagggcg cgcgcctcct ccaggccgcc ttcgcggccg cgcgctgccg
1621 cccaccctcc gtactcctca tcagcgagct agaggcgctg ctcccgccc gggacgacgg
1681 cgcggcggca gggggcgcgc tgcaggtgcc gctcctggcc tgcctggacg ggggctgcgg
1741 cgcgggggct gacggcgtgc tggttgtggg caccacctcg cggcccgcgg ctctggacga
1801 ggcgacccgc cggcgcttct ctctccgctt ctacgtggcg ctgcccgaca gcccggcccg
1861 cgggcagatc ctgcagcggg cgctggccca gcagggctgc gcgctcagtg agcgggaact
1921 ggcggcgctg gtgcagggca cgcagggctt ctctgggggc gagctgggc agctgtgcca
1981 gcaggcggcg gccggggcgg gcctcccggg gctgcagcgc ccctctcct acaaggacct
2041 ggaggcggcg ctggccaagg tgggcctag gcctctgcc aaggaactgg actcgttcgt
2101 ggagtgggac aaaaatgtacg gctccggaca ctgacggcgc gcgggggagg ccgcgggagc
2161 cgcagtccct ccgtccccgc cgcctccgcg tgggagggat gtcactgact aaacccggct
2221 ggcagggct ggagtggtga atgtgggatc ggggacagga ggggtctgcc ggtggatatt
2281 ttttttttcg tgggaaggaa aatgcttctg ccaggcagat gccatatgcg ccgtgtactc
2341 aggttttttcc tatttattgt ggactggaag ctcgccatct ccgcccggca gaccgggcag
2401 atccggcatg ggctggcacc cggggcctta agaactcctg ctctcttgcc acaacgcttt
2461 tgtctcctcg ctatctgaat ggcaccctcc ttctccctca ctctctccat cccattctct
2521 gcattctctt ggttttctct ccctttttgct ttgtcgctga caccccctgcc caccccatgc
2581 tggccctgtt tctctcctgc ccctccctcc ccagctctcc atccctcacc ctctgtgctt
2641 ctgtctccat ccctggctct ccagcgtccc tggccttttg gtccctgagc tttaatgcct
2701 ttccctgcct tctgttctta tttggactgc agtggccctt tgcaggagct ctggaggccc
```

```
2761 aggggctgag gaggagggtt acccctctac ccatctgaaa cctagggtct aggggggatca
2821 aggaaaaaaa gtccccaaag aagggggaatt ttttgtttgt ttttgagggg agatcccaga
2881 aatgtagctt gtttcatatt ttagtcttct tattttgta aaatgtgtag aatttgctgt
2941 ttttctttt cttttgacaa ctcaggaaga aactgacctc agaaagaatg ttagactttg
3001 gctgctctcc tgtgtgcccc tcacacctgc cccctccccc ccactccatc caggggacca
3061 aattctccca gacactcaaa aaatgagact tacggggaag gggagaggaa gacccagagg
3121 cctcagtgaa accccagcta ttcctggtca gaagcagaat gtattcctaa gggcttcctc
3181 cccagggccg aggcctaggc atgaatgtgg ggagtgggct gtggggtttg agagaaggga
3241 ggccttattc ctctcctgct gctccccacc ccctgcccca cccaacccct ccgctgagtg
3301 ttttctgtga agggctatcc agagttagga tgcccttgcc caattccttc ctgagaccca
3361 gaaggtaggg tgggagggcc caaatgggaa ggtgacctaa gcagaaagtc tccagaaagg
3421 tcatgtcccc tggccctgcc ttggcagagg tccccagtga cttatgctag gaggattcca
3481 tctgggtaga cagtctggcc acaaaatcag ctactggacc tcagccatct ctgctggagg
3541 ctctgaggag gagtgagcat ccctcacttg tgggggctct gtgaggaaat gtgccttccc
3601 cattcccccg gagtcctagg tctggagctc cagggctggg agaggtgag ggagatgggc
3661 aggggtgttt tctctgacct tggggggctta gtctcagtcc tgcctgaact ttccactagg
3721 cttggaaccc ttccaagaac catatttctc tccttcccac caattttccc ttgatgaggc
3781 tttagcagtt tgctcccacc accccagcc catttcacaa ctctgatctt agtccaaagc
3841 aggggacacg cccccccacc accttttt ctctctccca tctcagcctc ctgtgcagtt
3901 ccttgcctgc ccgtgcattt cctagagtct actgcctccc ccctggctgg gagggtgtct
3961 gggggggatc tttcagggc cctggcaccc agggcctgtg ctggcctagg agtgctgacc
4021 agaaggctgc tctgttcccc cccaccccg ttgctttctg gcccctctt tggagccagc
4081 cacccacagg gctttggtgc ctcagaagca gtgggctgcc gggtcacagc cgcaggctgc
4141 aaaagaccct cggagggagc atggagtgag gggttctctc tcaggtgtgt atgtattggg
4201 gggtgggggt gggtggaggg tgtcaggaa gttggggtgg gatcccagcc ttcccttcaa
4261 gaggcaggga gctctgggag gtggagtccc caccgctttc tctactaggc tcctcctgtt
4321 ccccaggctt ggggagcttt gcacaaggag actgcccccca gcctagtggc acctacctca
4381 tgggctctgg ggcaggtagg ggaagggcca gtccagctct ggtaatgctg ggggggaggca
4441 taccaaagaa tccaggggca gggagtgggg agggtgactt ccgagctggc ctctcccctt
4501 cctctaccca gactggggct gggatcctct cctcccgctg taaccatttc tacctcattt
4561 tgctgcgtgt tgtacatgga cgtatttatc tcctgtctga cgatgctctg cagttgtggt
4621 ctgtctacct cagaagagac tgtatttaa aagaaagtat tacacagtat taaagcgatg
4681 acatgtggtt tgcaaaaaaa aaaaaaaaa a
``` which encodes:

(SEQ ID NO: 2)
MHWTPEHAQPLNQWPEQHLDVSSTTPSPAHKLELPPGGRQRCHYAWAHD
DISALTASNLLKRYAEKYSGVLDSPYERPALGGYSDASFLNGAKGDPEP
WPGPEPPYPLASLHEGLPGTKSGGGGGSGALGGSPVLAGNLPEPLYAGN
ACGGPSAAPEYAAGYGGGYLAPGYCAQTGAALPPPPPAALLQPPPPPGY
GPSAPLYNYPAGGYAAQPGYGALPPPPGPPPAPYLTPGLPAPTPLPAPA
PPTAYGFPTAAPGAESGLSLKRKAADEGPEGRYRKYAYEPAKAPVADGA
SYPAADNGECRGNGFRAKPPGAAEEEASGKYGGGVPLKVLGSPVYGPQLE
PFEKFPERAPAPRGGFAVPSGETPKGVDPGALELVTSKMVDCGPPVQWA
DVAGQGALKAALEEELVWPLLRPPAYPGSLRPPRTVLLFGPRGAGKALL
GRCLATQLGATLLRLRGATLAAPGAAEGARLLQAAFAAARCRPPSVLLI
SELEALLPARDDGAAAGGALQVPLLACLDGGCGAGADGVLVVGTTSRPA

-continued

```
ALDEATRRRFSLRFYVALPDSPARGQILQRALAQQGCALSERELAALVQ

GTQGFSGGELGQLCQQAAAGAGLPGLQRPLSYKDLEAALAKVGPRASAK

ELDSFVEWDKMYGSGH.
(human Fidgetin-like 2)
```

In embodiments, the siRNA comprise one of the following pairs of sense/antisense sequences:

```
Sense:
                                        (SEQ ID NO: 3)
UUACACAGUAUUAAAGCGAUU Antisense:
                                        (SEQ ID NO: 4)
5' UCGCUUUAAUACUGUGUAAUU;
or Sense:
                                        (SEQ ID NO: 5)
CAUCUGAAACCUAGGGUCUUU Antisense:
                                        (SEQ ID NO: 6)
5' AGACCCUAGGUUUCAGAUGUU;
or Sense:
                                        (SEQ ID NO: 7)
GUGACUUAUGCUAGGAGGAUU Antisense:
                                        (SEQ ID NO: 8)
5' UCCUCCUAGCAUAAGUCACUU;
or Sense:
                                        (SEQ ID NO: 9)
GGUCAGAAGCAGAAUGUAUUU Antisense:
                                       (SEQ ID NO: 10)
5' AUACAUUCUGCUUCUGACCUU.
```

In an embodiment, the siRNA is double-stranded and comprises SEQ ID NO:3 and 4; SEQ ID NO:5 and 6; SEQ ID NO:7 and 8; or SEQ ID NO:9 and 10.

In an embodiment, the 5' terminal residue of a strand of the siRNA is phosphorylated. In an embodiment the 5' terminal residue of the antisense strand of the siRNA is phosphorylated.

As used herein an "aptamer" is a single-stranded oligonucleotide or oligonucleotide analog that binds to a particular target molecule, such as a Fidgetin-like 2 protein, or to a nucleic acid encoding a Fidgetin-like 2 protein, and inhibits the function or expression thereof, as appropriate. Alternatively, an aptamer may be a protein aptamer which consists of a variable peptide loop attached at both ends to a protein scaffold that interferes with Fidgetin-like 2 protein interactions The present invention provides kits for treating wounds, preferably skin wounds.

A composition provided in such a kit may be provided in a form suitable for reconstitution prior to use (such as a lyophilized injectable composition) or in a form which is suitable for immediate application to a wound, including to the wound margin, such as a lotion or ointment.

In an embodiment of the invention the inhibitor of fidgetin-like 2 is provided by a subcutaneous implant or depot medicament system for the pulsatile delivery of the inhibitor to a wound or site where a wound is to expected be formed to promote wound healing. The inhibitor can be provided, for example, in a therapeutically effective amount to each centimeter of a wound margin or each centimeter of a site at which a wound is expected to be formed.

A medicament in accordance with this aspect of the invention may be formulated in any appropriate carrier. Suitable carriers are pharmaceutically acceptable carriers, preferably those consistent with administration topically or administration by injection.

It will be appreciated that, while the inhibitor of Fidgetin-like 2 may be administered by the same route and in the same form in each incidence of treatment, different incidences of treatment may provide the inhibitor of Fidgetin-like 2 by different medicaments and/or different routes of administration. In embodiments of the invention the initial incidence of treatment may provide the inhibitor of Fidgetin-like 2 by means of an injection, such as an intradermal injection, while the second (and any subsequent) incidences of treatment may involve provision of the inhibitor of Fidgetin-like 2 by alternative routes, such as topical formulations, or vice versa. In an embodiment, multiple administrations of the inhibitor of Fidgetin-like 2 may be effected by the same means or route.

The benefits that may be derived from the present invention may be applicable to wounds at sites throughout the body. However, it may be preferred that the wound for which healing is promoted is a skin wound. For illustrative purposes the embodiments of the invention will generally be described with reference to skin wounds, although they remain applicable to other tissues and organs. Merely by way of example, in another preferred embodiment the wound may be a wound of the circulatory system, particularly of a blood vessel. Other wounds in which wound healing may be promoted in accordance with the present invention include as a result of surgery or as a result of a burn. Other wounds in which wound healing may be promoted in accordance with the present invention include skin ulcers caused by pressure, venous stasis, or diabetes mellitus.

In a non-limiting embodiment the inhibitor of Fidgetin-like 2 is provided in a bulk-eroding system such as polylactic acid and glycolic acid (PLGA) copolymer based microspheres or microcapsules systems containing the inhibitor of Fidgetin-like 2. In an embodiment, blends of PLGA:ethylcellulose systems may be used as an appropriate carrier. A further medicament in accordance with this aspect of the invention may be formulated in a surface-eroding system wherein the inhibitor of Fidgetin-like 2 is embedded in an erodible matrix such as the poly(ortho) ester and polyanhydride matrices wherein the hydrolysis of the polymer is rapid. A medicament in accordance with this aspect of the invention may also be formulated by combining a pulsatile delivery system as described above and an immediate release system such as a lyophilized injectable composition described above.

Examples of specific wounds in which healing may be promoted using the medicaments and methods of the invention include, but are not limited to, those independently selected from the group consisting of: wounds of the skin; wounds of the eye (including the inhibition of scarring resulting from eye surgery such as LASIK surgery, LASEK surgery, PRK surgery, glaucoma filtration surgery, cataract surgery, or surgery in which the lens capsule may be subject to scarring) such as those giving rise to corneal cicatrisation; wounds subject to capsular contraction (which is common surrounding breast implants); wounds of blood vessels; wounds of the central and peripheral nervous system (where prevention, reduction or inhibition of scarring may enhance neuronal reconnection and/or neuronal function); wounds of tendons, ligaments or muscle; wounds of the oral cavity, including the lips and palate (for example, to inhibit scarring resulting from treatment of cleft lip or palate); wounds of the internal organs such as the liver, heart, brain, digestive tissues and reproductive tissues; wounds of body cavities such as the abdominal cavity, pelvic cavity and thoracic cavity (where inhibition of scarring may reduce the number of incidences of adhesion formation and/or the size of adhesions formed); and surgical wounds (in particular wounds associated with cosmetic procedures, such as scar revision). It is particularly preferred that the medicaments and methods of the invention be used to promote healing of wounds of the skin.

The inhibitor may be used in a composition with additives. Examples of suitable additives are sodium alginate, as a gelatinizing agent for preparing a suitable base, or cellulose derivatives, such as guar or xanthan gum, inorganic gelatinizing agents, such as aluminum hydroxide or bentonites (termed thixotropic gel-formers), polyacrylic acid derivatives, such as Carbopol®, polyvinylpyrrolidone, microcrystalline cellulose and carboxymethylcellulose. Amphiphilic low molecular weight and higher molecular weight compounds, and also phospholipids, are also suitable. The gels can be present either as water-based hydrogels or as hydrophobic organogels, for example based on mixtures of low and high molecular weight paraffin hydrocarbons and vaseline. The hydrophilic organogels can be prepared, for example, on the basis of high molecular weight polyethylene glycols. These gelatinous forms are washable. Hydrophobic organogels are also suitable. Hydrophobic additives, such as petroleum jelly, wax, oleyl alcohol, propylene glycol monostearate and/or propylene glycol monopalmitostearate, in particular isopropyl myristate can be included. In an embodiment the inhibitor is in a composition comprising one or more dyes, for example yellow and/or red iron oxide and/or titanium dioxide for the purpose of matching as regards color. Compositions may be in any suitable form including gels, lotions, balms, pastes, sprays, powders, bandages, wound dressing, emulsions, creams and ointments of the mixed-phase or amphiphilic emulsion systems (oil/water-water/oil mixed phase), liposomes and transfersomes or plasters/band aid-type coverings. Emulsifiers which can be employed in compositions comprising the inhibitor of Fidgetin-like 2 include anionic, cationic or neutral surfactants, for example alkali metal soaps, metal soaps, amine soaps, sulphonated and sulphonated compounds, invert soaps, higher fatty alcohols, partial fatty acid esters of sorbitan and polyoxyethylene sorbitan, e.g. lanette types, wool wax, lanolin or other synthetic products for preparing the oil/water and/or water/oil emulsions.

Compositions comprising the inhibitor of Fidgetin-like 2 can also comprise vaseline, natural or synthetic waxes, fatty acids, fatty alcohols, fatty acid esters, for example as monoglycerides, diglycerides or triglycerides, paraffin oil or vegetable oils, hydrogenated castor oil or coconut oil, hog fat, synthetic fats (for example based on caprylic acid, capric acid, lauric acid or stearic acid, such as Softisan®), or triglyceride mixtures, such as Miglyol®, can be used as lipids, in the form of fatty and/or oleaginous and/or waxy components for preparing the ointments, creams or emulsions of the compositions comprising the inhibitor of fidgetin-like 2 used in the methods described herein.

Osmotically active acids and alkaline solutions, for example hydrochloric acid, citric acid, sodium hydroxide solution, potassium hydroxide solution, sodium hydrogen carbonate, may also be ingredients of the compositions and, in addition, buffer systems, such as citrate, phosphate, tris buffer or triethanolamine, for adjusting the pH. It is possible to add preservatives as well, such as methyl benzoate or propyl benzoate (parabens) or sorbic acid, for increasing the stability.

Pastes, powders and solutions are additional forms of compositions comprising the inhibitor of Fidgetin-like 2 which can be applied topically. As consistency-imparting bases, the pastes frequently contain hydrophobic and hydrophilic auxiliary substances, preferably, however, hydrophobic auxiliary substances containing a very high proportion of solids. In order to increase dispersity, and also flowability and slipperiness, and also to prevent agglomerates, the powders or topically applicable powders can, for example, contain starch species, such as wheat or rice starch, flame-dispersed silicon dioxide or siliceous earth, which also serve as diluent.

In an embodiment, the compositions comprise further active ingredients suitable for protecting or aiding in healing of the wound, for example one or more antibiotics, antiseptics, vitamins, anesthetics, antihistamines, anti-inflammatory agents, moisturizers, penetration-enhancing agents and/or anti-irritants.

In an embodiment of the methods and compositions described herein the subject is a mammal In an embodiment the subject is human.

As used herein, "promotion" of wound healing, or grammatical equivalent, means an acceleration in any one or more of visual appearance of wound recovery, reduction in wound size, reduction in distance between wound margins, scab formation, fibroplasia and re-epithelialization as compared to the corresponding parameter in an untreated wound.

As used herein, "wound" is a break or discontinuity in the structure of an organ or tissue (including skin), which includes epithelium, connective tissue, and muscle tissue, caused by an external agent. Examples of wounds include, but are not limited to, skin wounds, ulcerations, bedsores, grazes, tears, cuts, punctures, tympanic membrane perforations, burns, and those that are a consequence of plastic surgery procedures.

With regard to the methods described herein to identify candidate agents as inhibitors of Fidgetin-like 2, one skilled in the art can readily screen libraries of compounds, for example small molecule libraries, using the methods as described to identify agents which are inhibitors of Fidgetin-like 2 and which are therapeutic in treating wounds and promoting the healing of wounds. In addition, one skilled in the art can employ the method to identify peptides, peptidomimetics, antibodies, antibody fragments and nucleic acids which are inhibitors of Fidgetin-like 2 and which are therapeutic in treating wounds and promoting the healing of wounds.

The method can be employed as an assay using detection and quantification techniques known in the art, including those pertaining to measuring enzyme activity, such as the ATPase activity of Fidegtin-like 2.

The methods can be used to identify inhibitors of Fidgetin-like 2 which can then be applied to wound models to determine if the agent promotes/accelerates wound healing, especially for skin.

Preferably the inhibitor is biomembrane-permeable or is conjugated or otherwise attached to a moiety which renders the inhibitor biomembrane-permeable.

A method is also provided for treating wound in a subject comprising administering to the subject an amount of an inhibitor of Fidgetin effective to treat the wound. In an embodiment, the inhibitor of Fidgetin is a nucleic acid. In an embodiment, the inhibitor of Fidgetin is an siRNA or shRNA. In an embodiment, the nucleic acid is directed against a DNA or mRNA encoding Fidgetin. In an embodiment, the Fidgetin is human Fidgetin. In an embodiment, the wound is a neuronal wound. In an embodiment, the inhibitor of Fidgetin is encapsulated in a nanoparticle. In an embodiment, the nanoparticle is a liposomal nanoparticle. In an embodiment, the Fidgetin comprises the following sequence:

(SEQ ID NO: 11)

```
  1 MISSTSVYGL KMQWTPEHAQ WPEQHFDITS TTRSPAHKVE AYRGHLQRTY QYAWANDDIS

61 ALTASNLLKK YAEKYSGILE GPVDRPVLSN YSDTPSGLVN GRKNESEPWQ PSLNSEAVYP

121 MNCVPDVITA SKAGVSSALP PADVSASIGS SPGVASNLTE PSYSSSTCGS HTVPSLHAGL

181 PSQEYAPGYN GSYLHSTYSS QPAPALPSPH PSPLHSSGLL QPPPPPPPPP ALVPGYNGTS

241 NLSSYSYPSA SYPPQTAVGS GYSPGGAPPP PSAYLPSGIP APTPLPPTTV PGYTYQGHGL

301 TPIAPSALTN SSASSLKRKA FYMAGQGDMD SSYGNYSYGQ QRSTQSPMYR MPDNSISNTN

361 RGNGFDRSAE TSSLAFKPTK QLMSSEQQRK FSSQSSRALT PPSYSTAKNS LGSRSSESFG

421 KYTSPVMSEH GDEHRQLLSH PMQGPGLRAA TSSNHSVDEQ LKNTDTHLID LVTNEIITQG

481 PPVDWNDIAG LDLVKAVIKE EVLWPVLRSD AFSGLTALPR SILLFGPRGT GKTLLGRCIA

541 SQLGATFFKI AGSGLVAKWL GEAEKIIHAS FLVARCRQPS VIFVSDIDML LSSQVNEEHS

601 PVSRMRTEFL MQLDTVLTSA EDQIVVICAT SKPEEIDESL RRYFMKRLLI PLPDSTARHQ

661 IIVQLLSQHN YCLNDKEFAL LVQRTEGFSG LDVAHLCQEA VVGPLHAMPA TDLSAIMPSQ

721 LRPVTYQDFE NAFCKIQPSI SQKELDMYVE WNKMFGCSQ.
```

In an embodiment, the Fidgetin is encoded by a nucleic acid sequence comprising the following:

(SEQ ID NO: 12)

```
   1 gggtttgaaa ttccaacatg gcagaggctg cagtccgtct tcccttcaaa aacttggaat 61 gatttcaaat cataggcacc ttcacttaac cctagcttcc attcatcagc aaacacatcg 121 gatcgatgct acgctaacct atcgggttct ctctccgcgc gttcaggtta atgaatacc 181 tgacgaaagg gcccacgttt caaggcagtg acatttgata gctgagagga aaagtggctt 241 taatgaaaag caacctttgg aattcctgct tgtgagaaat ccaattcagc tttttgtgct 301 gccagcaaga aatgatcagt agcaccagtg tttatggctt gaagatgcag tggacgccag 361 agcatgccca gtggccagaa cagcactttg acatcacctc aaccactcgg tctcctgccc 421 acaaagttga agcctacaga ggtcatctgc agcgcaccta tcagtacgcc tgggcgaatg 481 atgacatatc tgctctgact gcatccaacc tactaaaaaa atatgcagag aagtattccg 541 gcattttgga aggtcctgtg gaccgacccg tactcagcaa ctattcggac acaccatcag 601 gactagtgaa cggtcggaaa atgaaagtg aaccctggca gccttccttg aattcagaag 661 ctgtttatcc catgaactgt gttccggatg ttatcactgc cagcaaagct ggagtcagtt 721 cagccctccc tccagcagat gtctctgcga gtataggaag ctctcctggg gtagccagca 781 acctgacaga acctagttat tcaagtagta cctgtggaag ccacactgta cccagtcttc 841 atgcagggct cccatctcag gaatatgccc caggatacaa cggatcatat ttgcattcta 901 cttatagtag ccagccagca cctgcacttc cttcacctca tccgtctcct ttgcatagct 961 ctgggctact acagccccca ccaccactc ctccgccacc agccttggtc ccaggctaca 1021 atgggacttc taacctctcc agttacagct atccgtctgc tagctatcct cctcagactg 1081 ctgtgggtc tgggtacagc cctgggggg caccgcctcc gccttcagcg tacctgcctt 1141 caggaattcc tgctcccacc cccctacccc ccaccactgt tcctggctac acctaccagg 1201 gccatggttt gacacctatt gcaccgtcgg ctctgacaaa cagttcagca agttctctca 1261 aaaggaaagc tttctacatg gcagggcaag gagatatgga ctccagttat ggaaattaca 1321 gctatggcca acagagatct acacagagtc ctatgtacag aatgcccgac aacagcattt 1381 caaacacaaa tcgggggaat ggctttgaca gaagtgctga acatcatcc ttagcattta
```

-continued

```
1441 agccaacgaa gcagctaatg tcctctgaac agcaaaggaa attcagcagc cagtccagta 1501 gggctctgac ccctccttcc tacagtactg ctaaaaattc attgggatca agatccagtg 1561 aatcctttgg gaagtacaca tcgccagtaa tgagtgagca tggggacgag cacaggcagc 1621 tcctctctca cccaatgcaa ggccctggac tccgtgcagc tacctcatcc aaccactctg 1681 tggacgagca actgaagaat actgacacgc acctcatcga cctggtaacc aatgagatta 1741 tcacccaagg acctccagtg gactggaatg acattgctgg tctcgacctg gtgaaggctg 1801 tcattaaaga ggaggtttta tggccagtgt tgaggtcaga cgcgttcagt ggactgacgg 1861 ccttacctcg gagcatcctt ttatttggac ctcgggggac aggcaaaaca ttattgggca 1921 gatgcatcgc tagtcagctg ggggccacat ttttcaaaat tgccggttct ggactagtcg 1981 ccaagtggtt aggagaagca gagaaaatta tccatgcctc ttttcttgtg ccaggtgtc 2041 gccagccctc ggtgattttt gttagtgaca ttgacatgct tctctcctct caagtgaatg 2101 aggaacatag tccagtcagt cggatgagaa ccgaatttct gatgcaactg acactgtac 2161 taacttcggc tgaggaccaa atcgtagtaa tttgtgccac cagtaaacca gaagaaatag 2221 atgaatccct tcggaggtac ttcatgaaac gactttaat cccacttcct gacagcacag 2281 cgaggcacca gataatagta caactgctct cacagcacaa ttactgtctc aatgacaagg 2341 agtttgcact gctcgtccag cgcacagaag gcttttctgg actagatgtg gctcatttgt 2401 gtcaggaagc agtggtgggc cccctccatg ccatgccagc cacagacctt tcagccatta 2461 tgcccagcca gttgaggccc gttacatatc aagactttga aaatgctttc tgcaagattc 2521 agcctagcat atctcaaaag gagcttgata tgtatgttga atggaacaaa atgtttggtt 2581 gcagtcagtg ataacttctt tagaaaaaaa aaatgtaatg aatgttggca cacacacata 2641 aaacctgcta catagggaat agagccccctt tccagtagag tttaaattgc aaagggtact 2701 ggggaagatg acgattaagt tgcatctta gagtcagggt agatttggag aaaagtgca 2761 tcaaatgaga gcttctgatt tgaaagcccc agatgacaga aagcatatgt ggatgctcag 2821 ttctgttcaa gctagacaac actcaccaag gagcaaggtg caagtgtgtt gatttcagaa 2881 ggacatgaac ctcgtgtgtt gattccattc tgctgttctc gagatttagt tgctgtcaag 2941 tgcctggagt ggtgctttat tttttgtttg cctcacaatt acattggtgg catgtgctaa 3001 tataaagagc tttaacttca acattattg gactaaagag atgaacagtt gtgttatgac 3061 agaaaaccag attttttgcca ttttaagagc aacagtattc ctcaatcctg tctgttctgc 3121 agtattaagc taagaacagg taaaacaggg taacggtaat ctggaccttta atttctgcag 3181 ttcatttctt ttaatgttct tgtctgcaaa aactcaggaa agtgattgtg atttgtacag 3241 tacctcaaag gaatgtgttg aaagcactat gtactgctga gagtaatagg ataggcttca 3301 atgttacttt atattaaaat gtatgtttac ctcaacaatt ggaaaatagc aaggaaaatt 3361 actttgaatg tatccagaaa aatactgaag tgtgatacaa ctgaatattt acagtttaaa 3421 gtagaaatgg aaggattttt ttaagttctt ttactaatta tggggaatta accagagcag 3481 aataattctt tatgtcaata actgcaagag ttcttagtac attgctcctt gataattaag 3541 tgaaaatgtt cttaaaaggt acactggtta attgaaagct acttattcag tttgtgttag 3601 tgtctagacc tgtcagccac aagacctgtt taggaccctg aaagtcacag tacctaaaaa 3661 ctatgactgc cttttttattg cataggtggt agtggtggtg atggtggtgg tagtttgcaa 3721 gttatctctt aaaactgctg ggaatggtgt cattctattc actaatctag cttatagact 3781 tgccgtgctg tttgatagaa tgcagaggat agcaaccaaa acaaatacac aaataaataa
```

```
-continued
3841 aaacaaaaac caaccaacaa accaacttac atacacatat atatatccac aaagaacctc 3901 tccatctcct cccttcttt ttgactccac tcttgtcagt gcaattttgc ttctcatttt 3961 gaaatctggg ctgtagtgct cctgctttat ttctacctca gttttgttac atttctcttg 4021 gaaagtaaag tagaaaattg gaagtggaca cacacactgc aatgtagctt gccaaacatg 4081 ttactttgtt ttcttccatc tttcaccgta aatctagttt ccaaagacat cagcatttgt 4141 gcttacttcc acctcagtct accagcccca cccctaccca tggcataagt ggcattttc 4201 ttaatttcct atttttctcc tgctctctgt caagttgttc tttgtatcct ttaatgcttt 4261 atgtgcaacc tttcattgat agtgggctga tgtttggcaa tgcttctgaa ctgtcacaga 4321 gcaggctgta gctttccaca gccactgccc atgcataagc agaacagcct ggccttttga 4381 atgtattttc ctgggttttt tcccctttc tttttttagt ttagagatgc agtaacaaaa 4441 ctgttgcaaa gcactggcat tttatgtatt caataaataa gtgatgtaca ttttaaaaa 4501 aatttaaata aatgcaatga gaagccccaa gaaag
```

All combinations of the various elements described herein are within the scope of the invention unless otherwise indicated herein or otherwise clearly contradicted by context.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

At present, papers have not been published on human Fidgetin-like 2, but the mouse homologue has been found to be highly expressed in most tissues (with the exception of testes) (Yang, Mahaffey et al. 2005). However, this laboratory has now identified the following role for human Fidgetin-like 2.

Results

Fidgetin-like 2 is expressed in human tissue culture cells where it localizes to microtubules. FIG. 1A shows a Western blot of human U2OS cell lysates probed with an anti-Fidgetin-like 2 antibody generated in lab. This antibody recognizes a single band that is substantially decreased by Fidgetin-like 2 siRNA treatment (see FIG. 2 below). FIG. 1B shows a migrating U2OS cell double-labeled for Fidgetin-like 2 and microtubules. At high magnification (inset), Fidgetin-like 2 clearly co-localizes with spans of the microtubule lattice near the cell edge.

Figure 2:
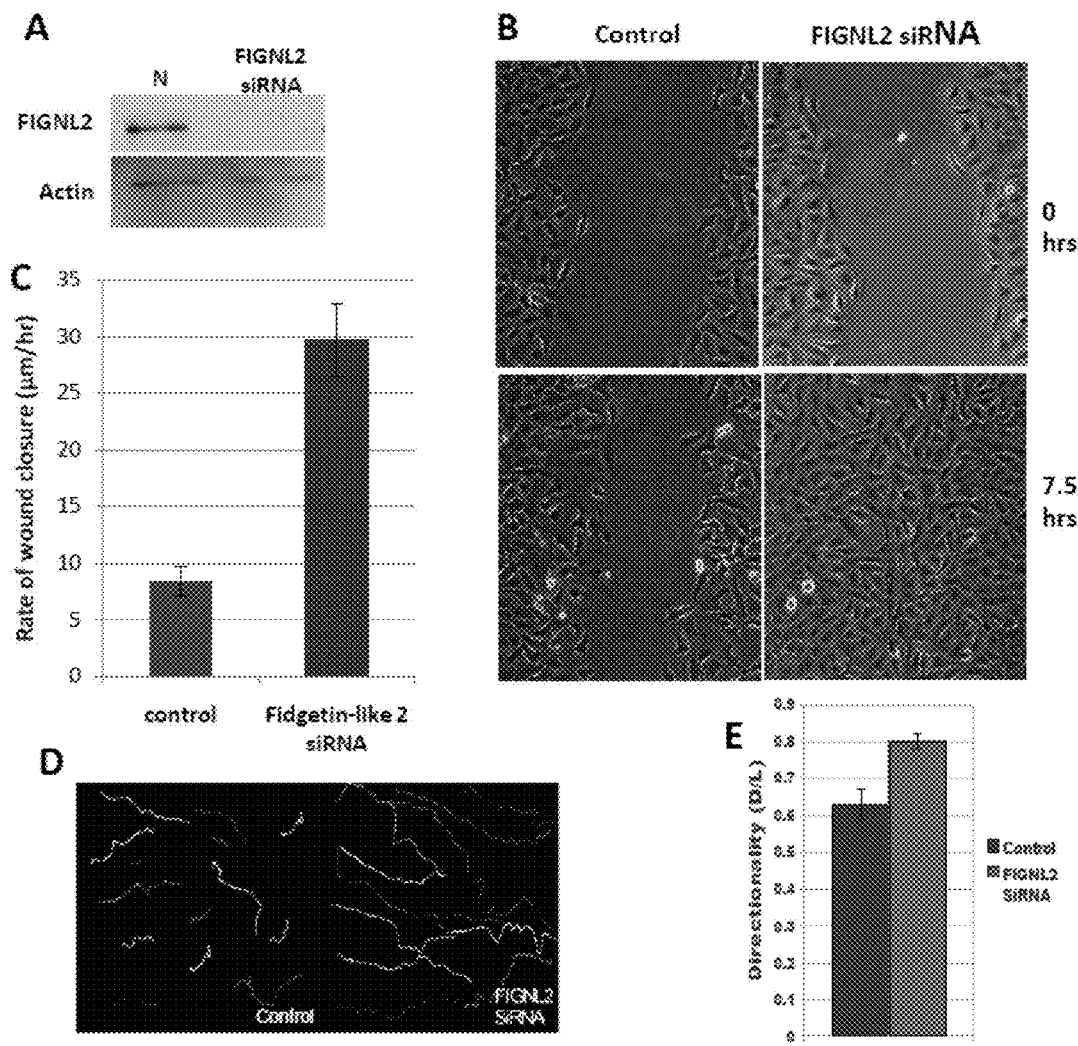
FIG. 2A-2E: Cells depleted of Fidgetin-like 2 display a several-fold increase in their rate of wound healing and migration.

Cells depleted of Fidgetin-like 2 display a several-fold increase in their rate of wound healing and migration (FIG. 2). FIG. 2A shows Western blots of U2OS cell lysates obtained from control (N) and Fidgetin-like 2 siRNA treated cultures (72 hrs after treatment). Actin was used as a loading control. FIG. 2B shows time-lapse phase contrast images of "wound healing" assays performed in control and Fidgetin-like 2 siRNA treated cultures. In these assays, a monolayer of U2OS cells is "wounded" by a pipette tip and the invasion of cells into the wound is monitored over time. FIG. 2C shows the average rate of wound closure in each condition which is increased nearly 4-fold after Fidgetin-like 2 siRNA. FIG. 2D shows the trajectories of single control and Fidgetin-like 2 siRNA treated cells as they enter the wound zone. Not only do Fidgetin-like 2 siRNA-treated cells move several-fold faster than controls, they also display more directionally persistent migration as indicated in FIG. 2E.

Figure 3:
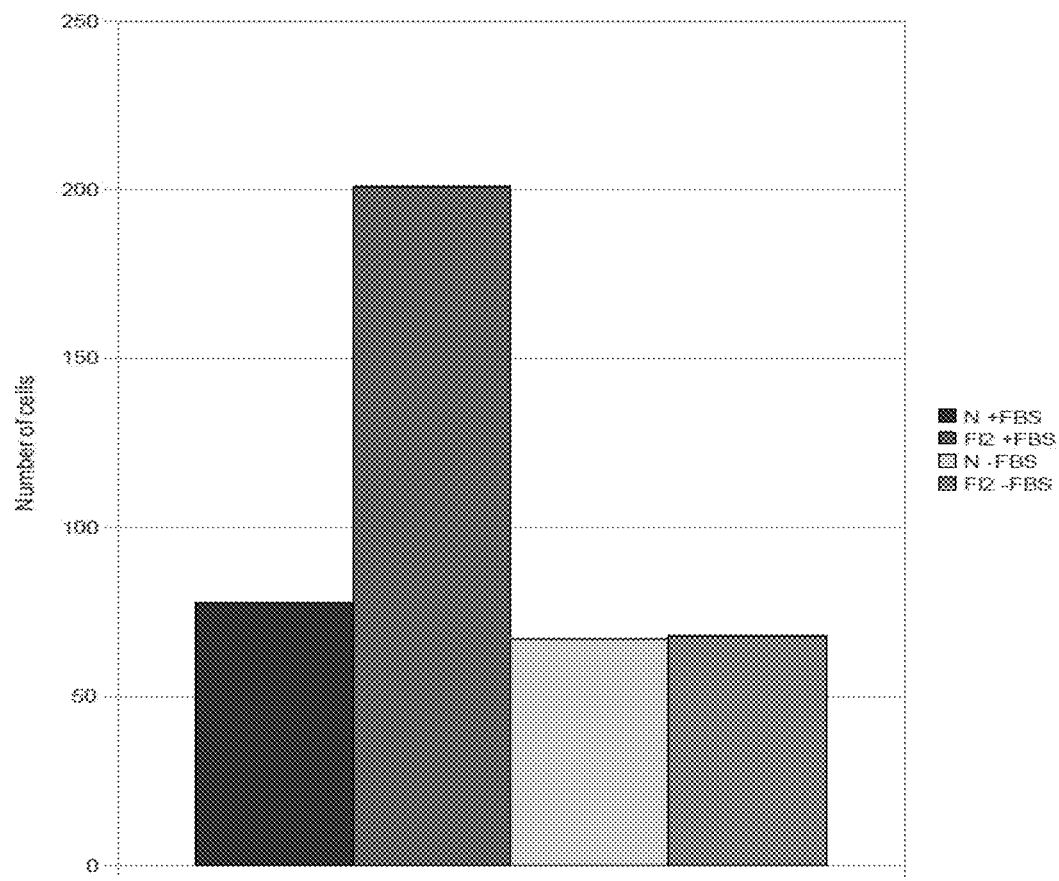
FIG. 3: Fidgetin-like 2 siRNA also dramatically enhances chemotaxis of cultured human cells. The impact of Fidgetin-like 2 siRNA on chemotaxis of human U2OS cells was measured in a transwell assay (modified Boyden chamber). This assay counts the number of cells that move through 8 µm pores towards a chemoattractant loaded in the distal well. The graph in FIG. 3 shows the number of control (N) and siRNA-treated (F12) cells that migrated through the pores before and three hours after the addition of a chemoattractant (Fetal Bovine Serum).

Fidgetin-like 2 siRNA also dramatically enhances chemotaxis of cultured human cells (FIG. 3). The impact of Fidgetin-like 2 siRNA on chemotaxis of human U2OS cells was measured in a transwell assay (modified Boyden chamber). This assay counts the number of cells that move through 8 μm pores towards a chemoattractant loaded in the distal well. The graph in FIG. 3 shows the number of control (N) and siRNA-treated (F12) cells that migrated through the pores before and three hours after the addition of a chemoattractant (Fetal Bovine Serum).

Figure 4:
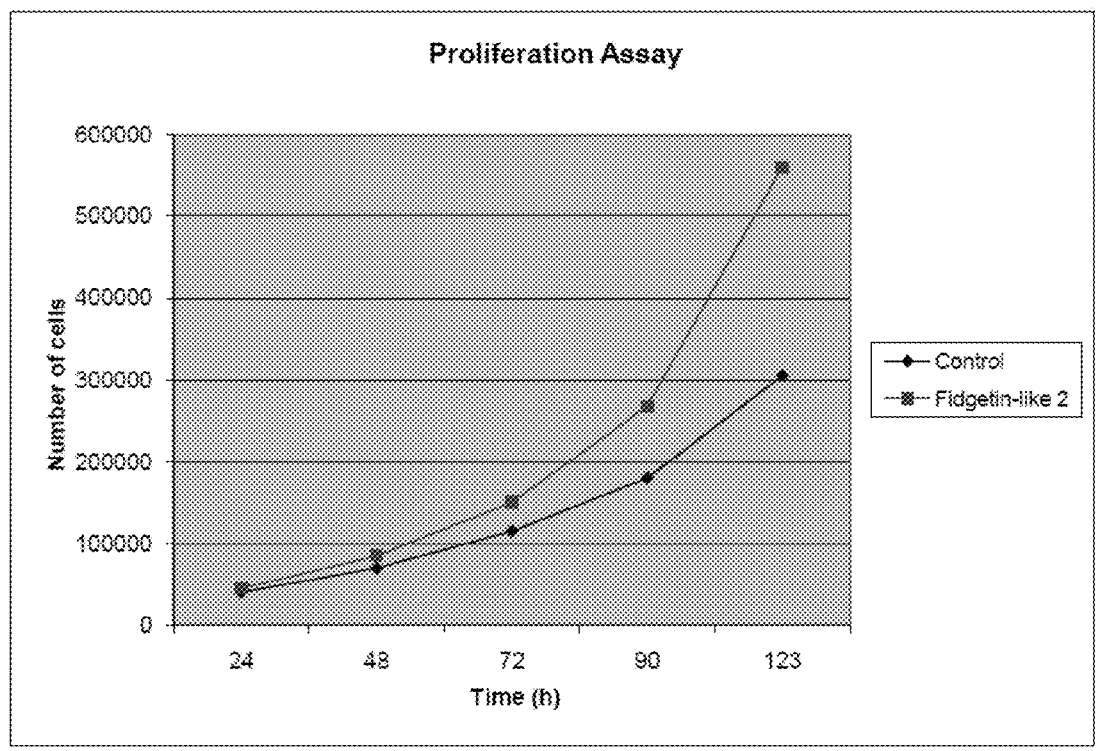
FIG. 4: siRNA directed to Fidgetin-like 2 elevates the rate of U2OS cell proliferation.
Figure 5:
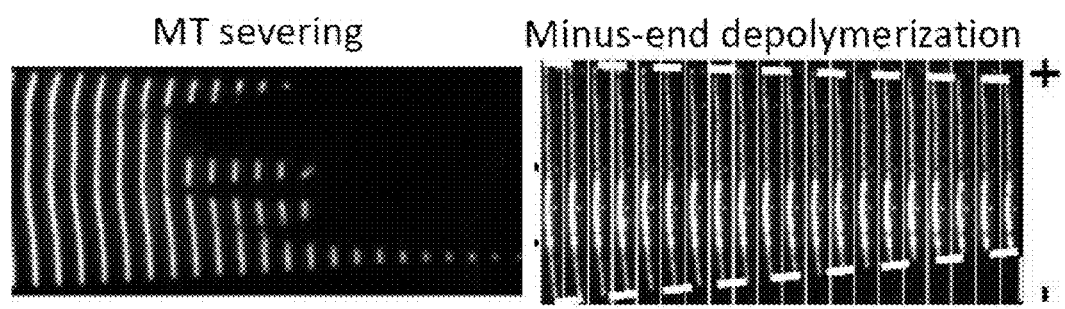
FIG. 5: Kymographs showing (left) severing of a MT incubated 50 nM recombinant Fidgetin and (right) depolymerization at the minus-end of a polarity marked induced MT incubated with 25 nM Fidgetin. ATP was added in both conditions. The reaction is entirely inhibited by the non-hydrolyzable ATP analogue, AMPPNP.
Figure 6:
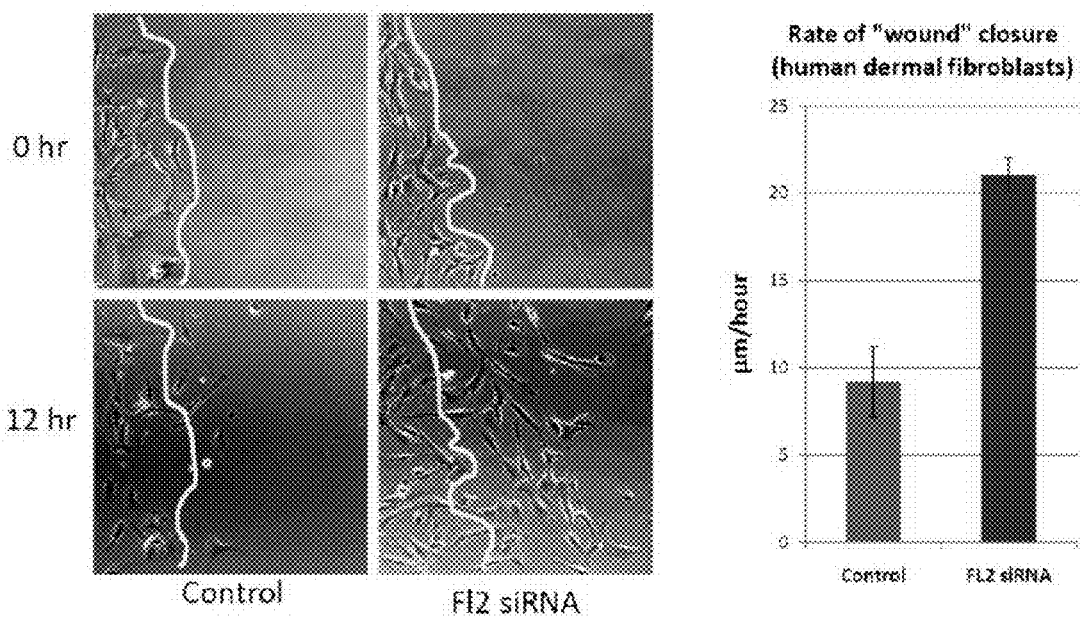
FIG. 6: Left panels show time-lapse phase contrast images of "wound healing" assays performed in control and Fidgetin-like 2 siRNA treated cultures of human dermal fibroblasts. In these assays, a monolayer is "wounded" by a pipette tip and the invasion of cells into the wound is monitored over time. The right panel shows the average rate of wound closure measured in each condition.

Fidgetin-like 2 siRNA elevates the rate of U2OS cell proliferation (FIG. 4). Although the biochemical activity of Fidgetin-like 2 has not been previously demonstrated, we have found that the closely related protein, Fidgetin, utilizes ATP hydrolysis to induce microtubule severing and depolymerization, in vitro (FIG. 5). FIG. 5 shows kymographs showing (left panel) severing of a MT incubated 50 nM recombinant Fidgetin and (right panel) depolymerization at the minus-end of a polarity marked induced MT incubated with 25 nM Fidgetin. ATP was added in both conditions. The reaction is entirely inhibited by the non-hydrolyzable ATP analogue, AMPPNP The studies of Fidgetin-like 2 were repeated in human dermal fibroblasts (adult). Fibroblasts depleted of Fidgetin-like 2 displayed a >2-fold increase in the rate of "wound closure" as determined by a standard scratch assay (see FIG. 6). The left panels of FIG. 6 show time-lapse phase contrast images of "wound healing" assays performed in control and Fidgetin-like 2 siRNA-treated cultures of human dermal fibroblasts. In these assays, a monolayer is "wounded" by a pipette tip and the invasion of cells into the wound is monitored over time. The right panel of FIG. 6 shows the average rate of wound closure measured in each condition.

Figures 7A, 7B:
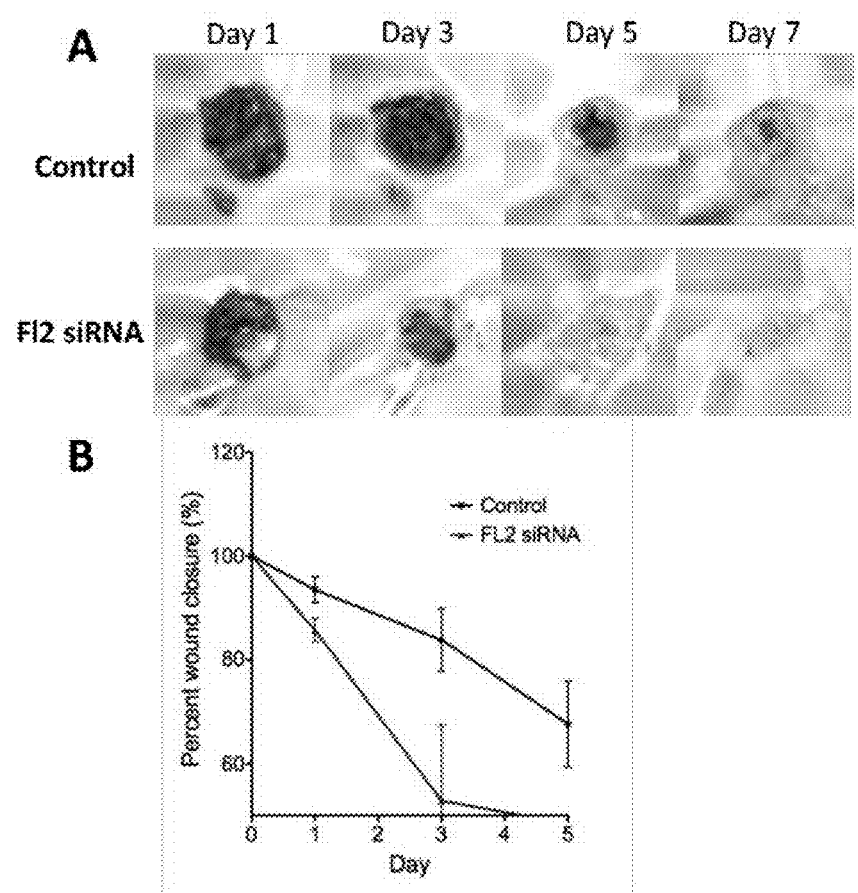
FIG. 7A-7B: Topical application of Fidgetin-like 2 siRNA encapsulated in nanpoparticles (np-si) increases the rate of wound closure in vivo. A) Images showing the closure of control and Fidgetin-like 2 np-si treated full thickness biopsy wounds positioned next to one another on the flank of a mouse. B) Plot showing the average rate of wound closure from each condition (n=3). Error bars are SEM. Wound closure is plotted to 50% because smaller wounds are difficult to measure with accuracy.
Figure 8:
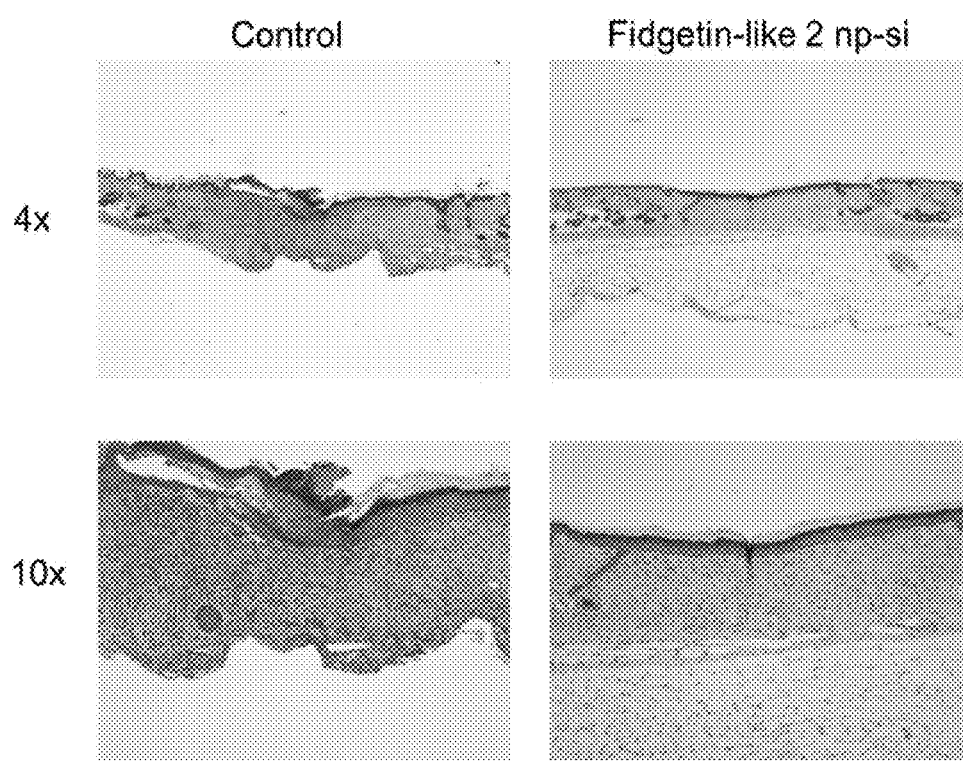
FIG. 8: Histology of Control and Fidgetin-like 2 np-si treated mouse biopsy wounds: Hematoxylin and Eosin staining of 5 mm punch biopsy wounds, mouse skin, day 9 after wounding. Control wounds (left) demonstrate a thin layer of re-epitheliazed epidermis with mounds of serum crust overlying. The dermis is composed of inflammatory, disorganized granulation tissue without evidence of subcutis. Fidgetin-like 2 np-si treated wounds demonstrate a completely re-epithelialized epidermis with overlying organized basket weaving stratum corneum. The dermis is devoid of intense inflammation and is infiltrated with parallel fibroblasts. There is a healthy appearing subcutis present.
Figure 9:
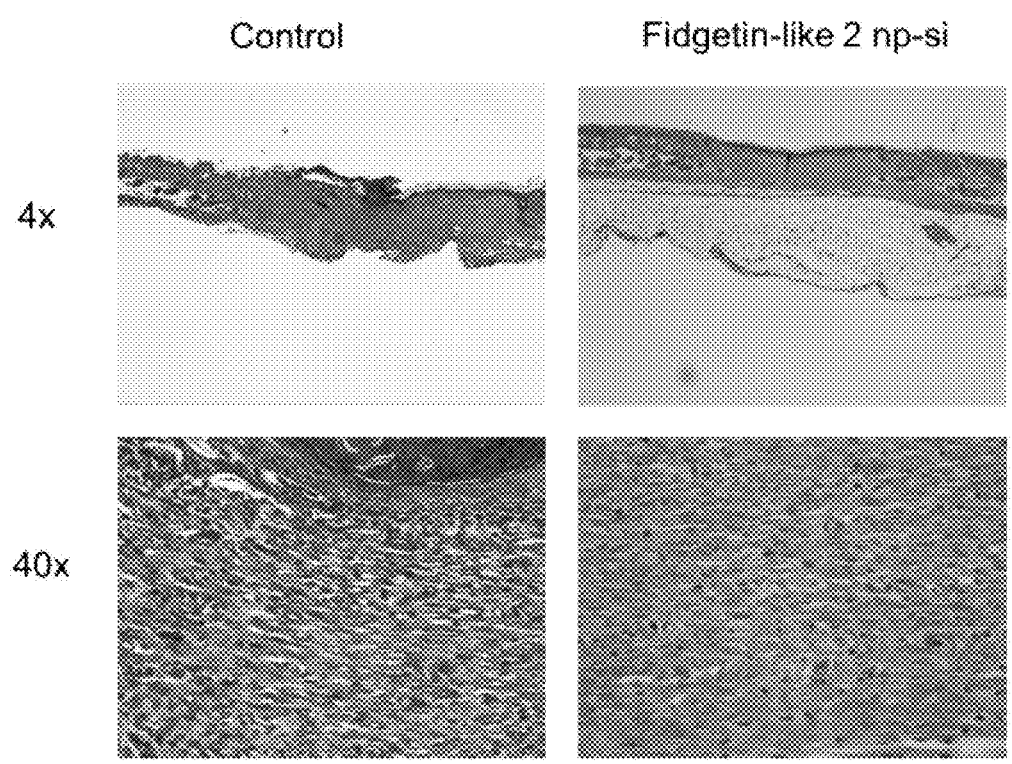
FIG. 9: Trichome masson staining for collagen reveal a necrobiotic degenerating collagen with minimal pale, newly deposited collagen present in the wound bed in the control (left) wound. In the Fidgetin-like 2 np-si treated wound, minimal cell death (as indicated by red) is noted and homogenous newly formed collagen (light blue) is noted.
Figure 10:
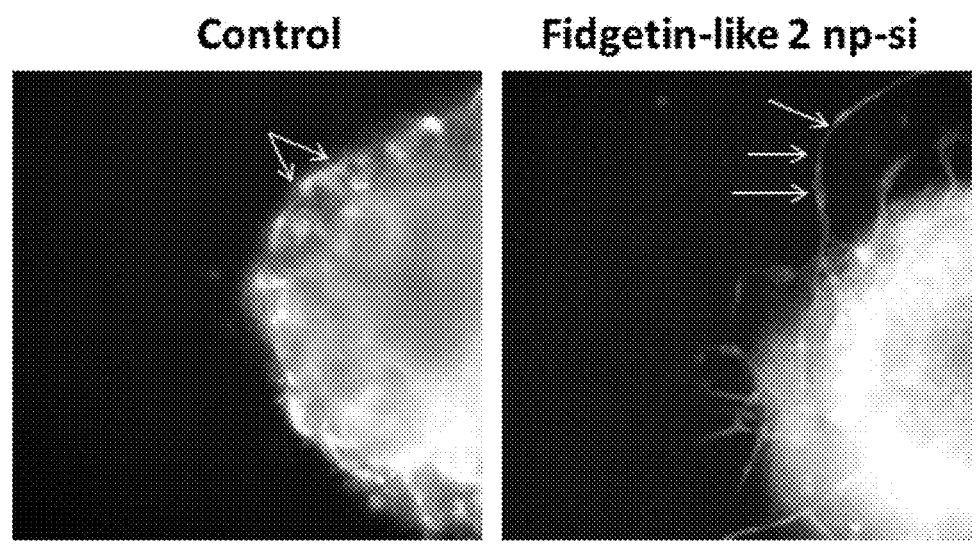
FIG. 10: Neoangiogenesis in embryonic hearts treated with Control or Fidgetin-like 2 np-si. Images show representative control and Fidgetin-like 2 np-si treated hearts three days after np-si treatment. In the control, migrating endocaridal cells (GFP-labeled) have penetrated the ventricular wall (arrows) and will undergo angiogenesis over the next several days. By contrast, Fidgetin-like 2 np-si treatment dramatically promotes the angiogenic process by the endocardial cells, which have already formed a fine vascular network at this time point (arrows).
Figure 11:
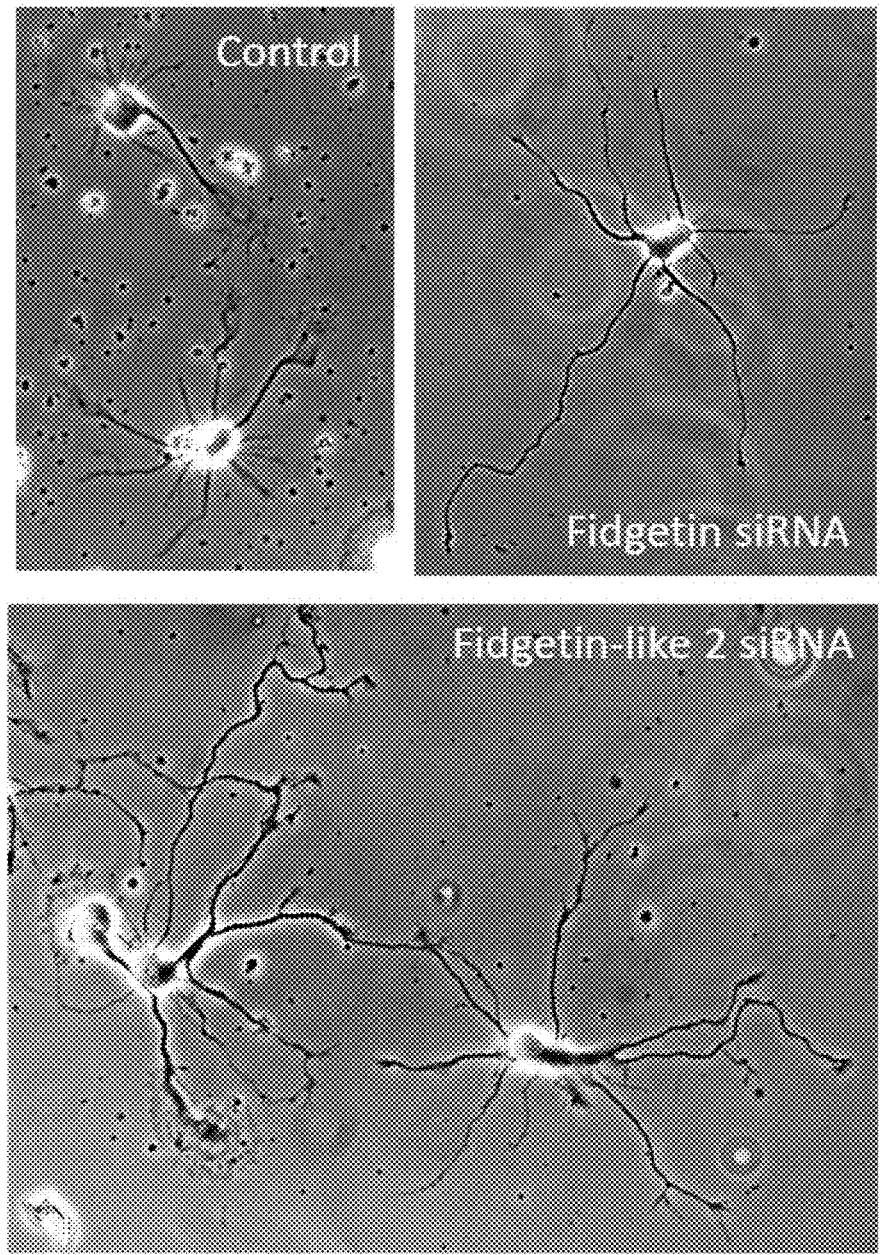
FIG. 11: Fidgetin and Fidgetin-like 2 siRNA nanoparticles strongly promote axon regrowth from hippocampal neurons. Images show dissociated rat hippocampal neurons 48 hours after siRNA treatment. (A similar effect was observed after 24 hours; not shown).
Figure 12:
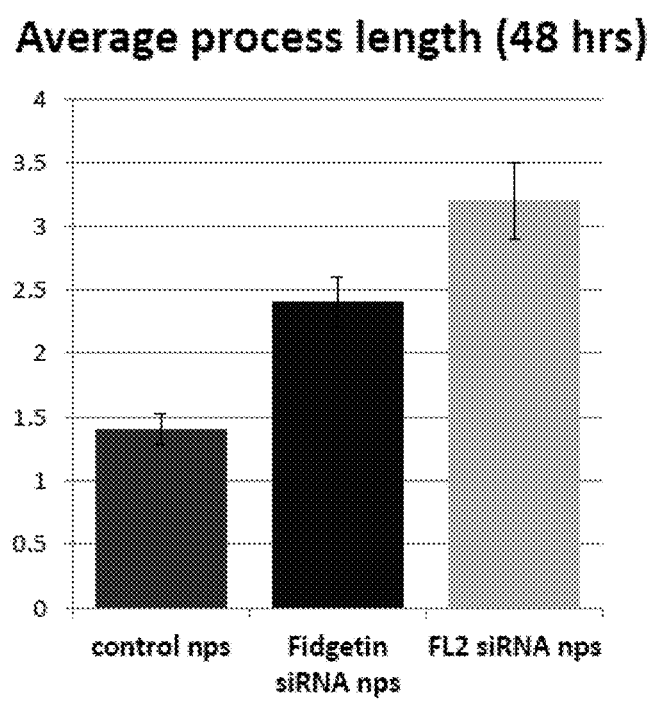
FIG. 12: Graphical representation showing Fidgetin and Fidgetin-like 2 siRNA nanoparticles strongly promote axon regrowth from hippocampal neurons.
Figure 13:
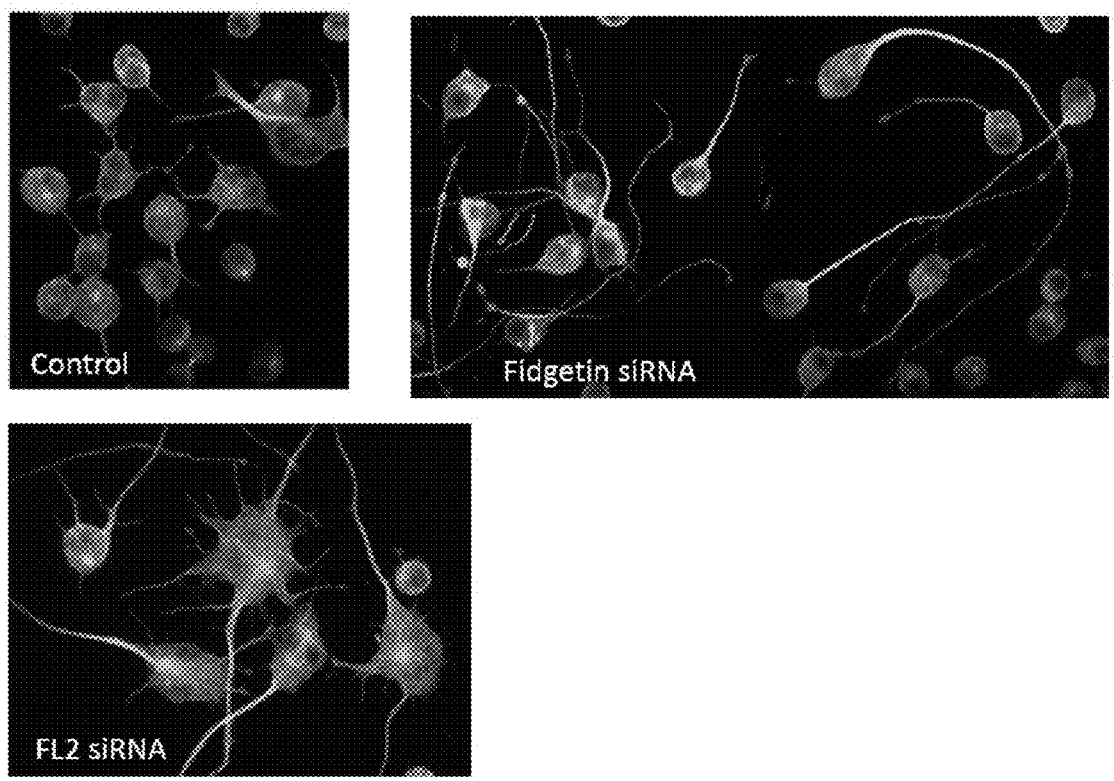
FIG. 13: Fidgetin and Fidgetin-like 2 siRNA nanoparticles promote axon growth and differentiation in N2A neuroblastoma cells (cells stained for microtubules).

In further experiments, topical application of Fidgetin-like 2 siRNA (encapsulated in nanoparticles) to mouse full thickness biopsy wounds was found to enhance wound healing (FIGS. 7, 8 and 9). In addition, depletion of Fidgetin-like 2 from embryonic mouse hearts was found to stimulate neoangiogenesis (FIG. 10). Furthermore, depletion of Fidgetin, and depletion of Fidgetin-like 2 from rat primary hippocampal neurons were both found to promote axon regrowth (FIGS. 11, 12 and 13).

EXAMPLE

A skin wound in a human subject is treated with a topically applied siRNA or shRNA which inhibits Fidgetin-like 2. The topically applied siRNA or shRNA is effective to treat the skin wound in the human subject. The topically applied siRNA or shRNA accelerates skin wound healing in the human subject.

References

Yang, Y., C. L. Mahaffey, et al. (2005). "Functional characterization of fidgetin, an AAA-family protein mutated in fidget mice." Exp Cell Res 304(1): 50-58.

What is claimed is:

1. A method of treating a wound in a subject comprising directly administering to a wound of the subject an amount of a siRNA or shRNA directed against a DNA or RNA encoding human Fidgetin-like 2 comprising the amino acid sequence set forth in SEQ ID NO:2 effective to treat a wound in a subject.

2. The method of claim 1, wherein the amount of the siRNA or shRNA directed against a DNA or RNA encoding human Fidgetin-like 2 is effective to accelerate wound healing.

3. The method of claim 1, wherein the siRNA or shRNA directed against a DNA or RNA encoding human Fidgetin-like 2 is administered topically to the wound.

4. The method of claim 1, wherein the siRNA is administered.

5. The method of claim 1, wherein the siRNA or shRNA is directed against an mRNA encoding the human Fidgetin-like 2.

6. The method of claim 4, wherein the siRNA comprises a sequence set forth in SEQ ID NOS:3, 4, 5, 6, 7, 8, 9, or 10.

7. The method of claim 1, wherein the wound is an epidermal wound.

8. The method of claim 1, wherein the wound is a skin wound.

9. The method of claim 1, wherein the wound is a cardiac tissue wound.

10. The method of claim 9, wherein the wound is a cardiovascular wound resulting from a myocardial infarction.

11. The method of claim 1, wherein the wound is a central nervous system wound or peripheral nervous system wound.

12. The method of claim 4, wherein the siRNA is encapsulated in a nanoparticle.

13. The method of claim 12, wherein the nanoparticle is a liposomal nanoparticle.

14. A method of treating a neuronal wound in a subject comprising administering directly to the wound in the subject an amount of a siRNA or shRNA directed against a DNA or an RNA encoding human Fidgetin encoded by the nucleic acid sequence set forth in SEQ ID NO:12 effective to treat a neuronal wound in a subject.

15. The method of claim 4, wherein the siRNA directed against a DNA or RNA encoding human Fidgetin-like 2 has at least one 2' sugar modification.

* * * * *